(12) United States Patent
Spohn et al.

(10) Patent No.: US 12,048,835 B2
(45) Date of Patent: Jul. 30, 2024

(54) FEATURES FOR ANGIOGRAPHY SYRINGE

(71) Applicant: Bayer HealthCare LLC, Whippany, NJ (US)

(72) Inventors: Michael Spohn, Fenelton, PA (US); Kevin Cowan, Allison Park, PA (US); Patrick Campbell, Pittsburgh, PA (US); Gerald Callan, Cranberry Township, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 18/041,104

(22) PCT Filed: Aug. 10, 2021

(86) PCT No.: PCT/US2021/045298
§ 371 (c)(1),
(2) Date: Feb. 9, 2023

(87) PCT Pub. No.: WO2022/035791
PCT Pub. Date: Feb. 17, 2022

(65) Prior Publication Data
US 2023/0310750 A1    Oct. 5, 2023

Related U.S. Application Data

(60) Provisional application No. 62/706,340, filed on Aug. 11, 2020, provisional application No. 63/073,519, filed on Sep. 2, 2020.

(51) Int. Cl.
*A61M 5/31* (2006.01)
*A61M 5/00* (2006.01)

(52) U.S. Cl.
CPC .......... *A61M 5/3134* (2013.01); *A61M 5/007* (2013.01)

(58) Field of Classification Search
CPC ...... A61M 5/3134; A61M 5/31; A61M 5/178; A61M 5/3129; A61M 5/007;
(Continued)

(56) References Cited

U.S. PATENT DOCUMENTS

| | | |
|---|---|---|
| 352,715 A | 11/1886 | Sandmark |
| 508,584 A | 11/1893 | Stevens |

(Continued)

FOREIGN PATENT DOCUMENTS

| | | |
|---|---|---|
| CN | 103917269 A | 7/2014 |
| CN | 105521533 A | 4/2016 |

(Continued)

OTHER PUBLICATIONS

International Preliminary Report on Patentability from PCT Application No. PCT/US2021/030210, Nov. 10, 2022.
(Continued)

*Primary Examiner* — Kevin C Sirmons
*Assistant Examiner* — Alexandra Lalonde
(74) *Attorney, Agent, or Firm* — Joseph L. Kent; James R. Stevenson; David Schramm

(57) ABSTRACT

A syringe including a proximal end, a distal end, and a cylindrical sidewall extending between the proximal end and the distal end, wherein the distal end comprises a conical distal end wall and a fluid nozzle at a distal end of the conical distal end wall; a cylindrical load bearing wall extending axially from the cylindrical sidewall past a proximal end of the conical distal end wall; and a plurality of radial ribs positioned around a periphery of the conical distal end wall, wherein a longitudinal axis of the plurality of radial ribs extends radially inward from the cylindrical load bearing wall towards the fluid nozzle over at least a portion of the conical distal end wall.

15 Claims, 8 Drawing Sheets

(58) Field of Classification Search
CPC ...... A61M 39/1011; A61M 2005/3132; A61M 5/00; A61M 5/142; A61M 5/145; A61M 5/1782; A61M 5/20; A61M 5/14546; A61M 5/34; A61M 5/344; A61M 5/343; A61M 5/345; A61M 2005/3142; A61M 2005/14288; A61M 2005/14553; A61M 2005/3103; A61M 2005/3114; A61M 2005/3117; A61M 2005/3118; A61M 2005/341; A61M 3/0287; A61M 2209/00; A61M 2205/10; A61M 2205/19; A61M 2205/58; A61M 2205/581; A61M 2205/583; A61M 5/1452; A61M 5/14566; A61M 2005/14573; A61M 2005/3131; A61B 90/05

See application file for complete search history.

(56) References Cited

U.S. PATENT DOCUMENTS

| | | | |
|---|---|---|---|
| 798,093 A | 8/1905 | Edward |
| 817,054 A | 4/1906 | Daniel |
| 937,029 A | 10/1909 | Blessing et al. |
| 945,143 A | 1/1910 | Iacques |
| 1,388,946 A | 8/1921 | Goold |
| 1,930,929 A | 10/1933 | Joel et al. |
| 2,062,285 A | 12/1936 | Sam et al. |
| 2,511,291 A | 6/1950 | Mueller |
| 2,514,575 A | 7/1950 | Hein et al. |
| 2,583,206 A | 1/1952 | Borck et al. |
| 2,592,381 A | 4/1952 | Blackman |
| 2,616,422 A | 11/1952 | Jones |
| 2,667,163 A | 1/1954 | Smith |
| 2,667,164 A | 1/1954 | Smith |
| 2,667,165 A | 1/1954 | Smith |
| 2,667,872 A | 2/1954 | Smith |
| 2,672,866 A | 3/1954 | Kater |
| 2,673,561 A | 3/1954 | Peterson, Jr. |
| 2,688,963 A | 9/1954 | Smith |
| 2,688,964 A | 9/1954 | Smith |
| 2,690,179 A | 9/1954 | Fox |
| 2,717,598 A | 9/1955 | Krasno |
| 2,805,662 A | 9/1957 | Lawshe et al. |
| 2,911,972 A | 11/1959 | Elinger |
| 2,915,986 A | 12/1959 | Sisson |
| 2,935,067 A | 5/1960 | Bouet |
| 2,950,717 A | 8/1960 | Bonet |
| 3,101,712 A | 8/1963 | Strazdins et al. |
| 3,155,281 A | 11/1964 | Stracey |
| 3,159,312 A | 12/1964 | Van Sciver, II |
| 3,161,194 A | 12/1964 | Chapman |
| 3,161,195 A | 12/1964 | Taylor et al. |
| 3,166,070 A | 1/1965 | Everett |
| 3,172,577 A | 3/1965 | Hartung |
| 3,190,619 A | 6/1965 | Penney et al. |
| 3,199,511 A | 8/1965 | Kulick |
| 3,231,139 A | 1/1966 | Bouet |
| 3,276,472 A | 10/1966 | Jinkens et al. |
| 3,301,293 A | 1/1967 | Santelli |
| 3,340,869 A | 9/1967 | Bane |
| 3,353,537 A | 11/1967 | Knox et al. |
| 3,390,821 A | 7/1968 | Mullan |
| 3,411,503 A | 11/1968 | Santomieri |
| 3,412,906 A | 11/1968 | Dinger |
| 3,442,424 A | 5/1969 | Sam et al. |
| 3,471,058 A | 10/1969 | Peter et al. |
| 3,473,524 A | 10/1969 | John |
| 3,474,844 A | 10/1969 | Rudolph et al. |
| 3,506,163 A | 4/1970 | Rauh et al. |
| 3,507,278 A | 4/1970 | Winfried |
| 3,527,215 A | 9/1970 | De Witt |
| 3,557,788 A | 1/1971 | Swartz |
| 3,613,963 A | 10/1971 | Berkmuller |
| 3,618,846 A | 11/1971 | Poli |
| 3,635,444 A | 1/1972 | Potter |
| 3,671,208 A | 6/1972 | Medsker |
| 3,699,961 A | 10/1972 | Szpur |
| 3,719,207 A | 3/1973 | Takeda |
| 3,736,932 A | 6/1973 | Satchell |
| 3,785,367 A | 1/1974 | Fortin et al. |
| 3,826,409 A | 7/1974 | Chilcoate |
| 3,868,967 A | 3/1975 | Harding |
| 3,873,003 A | 3/1975 | Seiferth et al. |
| 3,938,514 A | 2/1976 | Boucher |
| 3,998,223 A | 12/1976 | Dawe |
| 4,035,461 A | 7/1977 | Korth |
| 4,041,944 A | 8/1977 | Rhodes |
| 4,044,836 A | 8/1977 | Martin et al. |
| 4,064,879 A | 12/1977 | Leibinsohn |
| 4,066,080 A | 1/1978 | Sneider |
| 4,131,217 A | 12/1978 | Sandegren |
| 4,136,802 A | 1/1979 | Mascia et al. |
| 4,140,117 A | 2/1979 | Buckles et al. |
| 4,171,698 A | 10/1979 | Genese |
| 4,204,775 A | 5/1980 | Speer |
| 4,208,136 A | 6/1980 | King et al. |
| 4,236,516 A | 12/1980 | Nilson |
| 4,245,655 A | 1/1981 | Patel |
| 4,312,344 A | 1/1982 | Nilson |
| 4,318,400 A | 3/1982 | Peery et al. |
| 4,325,369 A | 4/1982 | Nilson |
| 4,329,067 A | 5/1982 | Goudy, Jr. |
| 4,349,129 A | 9/1982 | Amneus |
| 4,392,491 A | 7/1983 | Takasugi et al. |
| 4,411,656 A | 10/1983 | Cornett, III |
| 4,419,096 A | 12/1983 | Leeper et al. |
| 4,438,845 A | 3/1984 | Mochow |
| 4,441,823 A | 4/1984 | Power et al. |
| 4,444,310 A | 4/1984 | Odell |
| 4,526,296 A | 7/1985 | Berger et al. |
| 4,610,665 A | 9/1986 | Matsumoto et al. |
| 4,741,733 A | 5/1988 | Winchell et al. |
| 4,747,839 A | 5/1988 | Tarello et al. |
| 4,753,638 A | 6/1988 | Peters |
| 4,773,458 A | 9/1988 | Touzani |
| 4,824,145 A | 4/1989 | Carlsson |
| 4,850,807 A | 7/1989 | Frantz |
| 4,895,570 A | 1/1990 | Larkin |
| 4,898,588 A * | 2/1990 | Roberts ............... A61M 3/0287 604/242 |
| 4,904,239 A | 2/1990 | Winchell et al. |
| 4,952,068 A | 8/1990 | Flint |
| 4,969,879 A | 11/1990 | Lichte |
| 5,000,739 A | 3/1991 | Kulisz et al. |
| 5,011,477 A | 4/1991 | Winchell et al. |
| 5,026,348 A | 6/1991 | Venegas |
| 5,033,631 A | 7/1991 | Nightingale |
| 5,048,684 A | 9/1991 | Scott |
| 5,120,315 A | 6/1992 | Hessel |
| 5,147,311 A | 9/1992 | Pickhard |
| 5,163,928 A | 11/1992 | Hobbs et al. |
| 5,178,610 A | 1/1993 | Tsujikawa et al. |
| 5,192,272 A | 3/1993 | Faure |
| 5,199,567 A | 4/1993 | Discko, Jr. |
| 5,201,438 A | 4/1993 | Norwood |
| 5,209,372 A | 5/1993 | Norwood |
| 5,236,204 A | 8/1993 | Hempel |
| 5,237,309 A | 8/1993 | Frantz et al. |
| 5,238,003 A | 8/1993 | Baidwan et al. |
| 5,238,150 A | 8/1993 | Williams |
| 5,240,130 A | 8/1993 | Osbakk |
| 5,242,422 A | 9/1993 | Schneberger et al. |
| 5,263,940 A | 11/1993 | Kriesel |
| 5,269,428 A | 12/1993 | Gilbert |
| 5,312,018 A | 5/1994 | Evezich |
| 5,316,452 A | 5/1994 | Bogen et al. |
| 5,318,520 A | 6/1994 | Nakao |
| 5,318,540 A | 6/1994 | Athayde et al. |
| 5,333,761 A | 8/1994 | Davis et al. |
| 5,342,313 A | 8/1994 | Campbell et al. |
| 5,353,961 A | 10/1994 | Debush |
| 5,370,250 A | 12/1994 | Gilbert |
| 5,383,858 A | 1/1995 | Reilly et al. |

(56) References Cited

U.S. PATENT DOCUMENTS

| | | |
|---|---|---|
| 5,397,157 A | 3/1995 | Hempel et al. |
| 5,399,173 A | 3/1995 | Parks et al. |
| 5,431,185 A | 7/1995 | Shannon et al. |
| 5,492,147 A | 2/1996 | Challender et al. |
| 5,507,535 A | 4/1996 | McKamey et al. |
| 5,520,653 A | 5/1996 | Reilly et al. |
| 5,573,129 A | 11/1996 | Nagata et al. |
| 5,578,005 A | 11/1996 | Sancoff et al. |
| 5,584,413 A | 12/1996 | Jung |
| 5,592,948 A | 1/1997 | Gatten |
| 5,609,580 A | 3/1997 | Kwiatkowski et al. |
| 5,615,791 A | 4/1997 | Vatelot et al. |
| 5,638,995 A | 6/1997 | Mazda |
| 5,651,776 A | 7/1997 | Appling et al. |
| 5,683,369 A | 11/1997 | Tsukada |
| 5,725,500 A | 3/1998 | Micheler |
| 5,758,789 A | 6/1998 | Shin et al. |
| 5,794,107 A | 8/1998 | Russell |
| 5,827,233 A | 10/1998 | Futagawa et al. |
| 5,836,922 A | 11/1998 | Hansen et al. |
| 5,873,861 A | 2/1999 | Hitchins et al. |
| 5,893,843 A | 4/1999 | Rodrigues Claro |
| 5,899,889 A | 5/1999 | Futagawa et al. |
| 5,935,105 A | 8/1999 | Manning et al. |
| 5,957,898 A | 9/1999 | Jepson et al. |
| RE36,377 E | 11/1999 | Gilbert |
| 5,976,112 A | 11/1999 | Lyza, Jr. |
| 5,979,326 A | 11/1999 | Ohinata |
| 5,980,489 A | 11/1999 | Kriesel |
| 5,984,378 A | 11/1999 | Ostrander et al. |
| 6,054,194 A | 4/2000 | Kane |
| 6,056,724 A | 5/2000 | Lacroix |
| 6,062,437 A | 5/2000 | Mascitelli |
| 6,063,058 A | 5/2000 | Sakamoto |
| 6,077,252 A | 6/2000 | Siegel |
| 6,105,815 A | 8/2000 | Mazda |
| 6,132,396 A | 10/2000 | Antanavich et al. |
| 6,142,976 A | 11/2000 | Kubo |
| 6,159,183 A | 12/2000 | Neer et al. |
| 6,177,049 B1 | 1/2001 | Schnell et al. |
| 6,216,915 B1 | 4/2001 | Harman et al. |
| 6,224,577 B1 | 5/2001 | Dedola et al. |
| 6,250,505 B1 | 6/2001 | Petit |
| 6,270,482 B1 | 8/2001 | Rosoff et al. |
| 6,306,191 B1 | 10/2001 | McInerney et al. |
| 6,315,761 B1 | 11/2001 | Shcherbina et al. |
| 6,319,235 B1 | 11/2001 | Yoshino |
| 6,322,535 B1 | 11/2001 | Hitchins et al. |
| 6,322,542 B1 | 11/2001 | Nilson et al. |
| 6,328,715 B1 | 12/2001 | Dragan et al. |
| 6,332,876 B1 | 12/2001 | Poynter et al. |
| 6,442,418 B1 | 8/2002 | Evans, III et al. |
| 6,450,993 B1 | 9/2002 | Lin |
| 6,465,024 B1 | 10/2002 | Di et al. |
| 6,485,471 B1 | 11/2002 | Zivitz et al. |
| 6,497,684 B2 | 12/2002 | Witowski et al. |
| 6,558,358 B2 | 5/2003 | Rosoff et al. |
| 6,575,930 B1 | 6/2003 | Trombley, III et al. |
| 6,578,738 B1 | 6/2003 | Keller |
| 6,616,000 B1 | 9/2003 | Renz |
| 6,620,134 B1 | 9/2003 | Trombley, III et al. |
| 6,634,524 B1 | 10/2003 | Helmenstein |
| 6,643,537 B1 | 11/2003 | Zatezalo et al. |
| 6,652,489 B2 | 11/2003 | Trocki et al. |
| 6,702,143 B2 | 3/2004 | Wang |
| 6,716,195 B2 | 4/2004 | Nolan, Jr. et al. |
| 6,723,074 B1 | 4/2004 | Halseth |
| 6,726,657 B1 | 4/2004 | Dedig et al. |
| 6,731,971 B2 | 5/2004 | Evans et al. |
| 6,773,417 B2 | 8/2004 | Fitzgibbons et al. |
| 6,830,563 B1* | 12/2004 | Singer ............ A61M 25/00 604/181 |
| 6,840,164 B2 | 1/2005 | Eastman |
| 6,855,130 B2 | 2/2005 | Saulenas et al. |
| 6,866,039 B1 | 3/2005 | Wright et al. |
| 6,866,654 B2 | 3/2005 | Callan et al. |
| 6,869,419 B2 | 3/2005 | Dragan et al. |
| 6,921,384 B2 | 7/2005 | Reilly et al. |
| RE38,770 E | 8/2005 | Gilbert |
| 6,974,443 B2 | 12/2005 | Reilly et al. |
| 6,984,222 B1 | 1/2006 | Hitchins et al. |
| 7,004,213 B2 | 2/2006 | Hansen |
| 7,011,650 B2 | 3/2006 | Rosoff et al. |
| 7,094,216 B2 | 8/2006 | Trombley, III et al. |
| 7,101,352 B2 | 9/2006 | Duchon et al. |
| 7,192,416 B1 | 3/2007 | Lazzaro et al. |
| 7,192,549 B2 | 3/2007 | Hansen |
| 7,240,926 B2 | 7/2007 | Dalle et al. |
| 7,250,039 B2 | 7/2007 | Fitzgerald |
| 7,309,463 B2 | 12/2007 | Hansen |
| 7,351,221 B2 | 4/2008 | Trombley, III et al. |
| 7,419,478 B1 | 9/2008 | Reilly et al. |
| 7,427,281 B2 | 9/2008 | Uber et al. |
| 7,457,804 B2 | 11/2008 | Uber, III et al. |
| 7,462,166 B2 | 12/2008 | Kowan et al. |
| 7,497,843 B1 | 3/2009 | Castillo et al. |
| 7,513,378 B2 | 4/2009 | Mori et al. |
| 7,540,856 B2 | 6/2009 | Hitchins et al. |
| 7,553,294 B2 | 6/2009 | Lazzaro et al. |
| 7,556,619 B2 | 7/2009 | Spohn et al. |
| 7,563,249 B2 | 7/2009 | Schriver et al. |
| 7,581,559 B2 | 9/2009 | Bausmith et al. |
| 7,597,683 B2 | 10/2009 | Myhrberg et al. |
| 7,604,623 B2 | 10/2009 | Brunner et al. |
| 7,611,503 B2 | 11/2009 | Spohn et al. |
| 7,621,395 B2 | 11/2009 | Mogensen et al. |
| 7,666,169 B2 | 2/2010 | Cowan et al. |
| 7,686,788 B2 | 3/2010 | Freyman et al. |
| 7,766,883 B2 | 8/2010 | Reilly et al. |
| 7,802,691 B2 | 9/2010 | Musalek et al. |
| 7,818,992 B2 | 10/2010 | Riley et al. |
| 7,861,893 B2 | 1/2011 | Voegele et al. |
| 7,996,381 B2 | 8/2011 | Uber, III et al. |
| 8,057,406 B2 | 11/2011 | Mohiuddin |
| 8,147,464 B2 | 4/2012 | Spohn et al. |
| 8,162,903 B2 | 4/2012 | Reilly et al. |
| 8,337,456 B2 | 12/2012 | Schriver et al. |
| 8,388,580 B2 | 3/2013 | Schriver et al. |
| 8,419,676 B2 | 4/2013 | Evans et al. |
| 8,439,863 B2 | 5/2013 | Fago et al. |
| 8,521,716 B2 | 8/2013 | Uber, III et al. |
| 8,540,698 B2 | 9/2013 | Spohn et al. |
| 8,740,877 B2 | 6/2014 | Borlaug et al. |
| 8,795,240 B2 | 8/2014 | Chelak |
| 8,882,702 B2 | 11/2014 | Suchecki et al. |
| 8,882,708 B2 | 11/2014 | Hieb et al. |
| 8,919,384 B2 | 12/2014 | Spohn et al. |
| 8,945,051 B2 | 2/2015 | Schriver et al. |
| 8,992,489 B2 | 3/2015 | Spohn et al. |
| 9,173,995 B1 | 11/2015 | Tucker et al. |
| 9,180,252 B2 | 11/2015 | Gelblum et al. |
| 9,180,260 B2 | 11/2015 | Huang et al. |
| 9,199,033 B1 | 12/2015 | Cowan et al. |
| 9,474,857 B2 | 10/2016 | Riley et al. |
| 9,498,570 B2 | 11/2016 | Cowan et al. |
| 9,555,379 B2 | 1/2017 | Schriver et al. |
| 9,566,381 B2 | 2/2017 | Barron et al. |
| 9,649,436 B2 | 5/2017 | Capone et al. |
| 9,901,671 B2 | 2/2018 | Toews et al. |
| 10,022,493 B2 | 7/2018 | Shearer, Jr. et al. |
| 10,046,106 B2 | 8/2018 | Cowan et al. |
| 10,105,491 B2 | 10/2018 | Gelblum et al. |
| 10,124,110 B2 | 11/2018 | Dedig et al. |
| 10,188,849 B2 | 1/2019 | Fangrow |
| 10,201,666 B2 | 2/2019 | Cowan et al. |
| 10,398,353 B2 | 9/2019 | Addison et al. |
| 10,420,902 B2 | 9/2019 | Cowan et al. |
| 10,507,319 B2 | 12/2019 | Haury et al. |
| 10,549,084 B2 | 2/2020 | Sokolov et al. |
| 10,857,345 B2 | 12/2020 | Uber, III et al. |
| 10,933,190 B2 | 3/2021 | Berry et al. |
| 11,083,882 B2 | 8/2021 | Schrauder et al. |
| 11,207,462 B2 | 12/2021 | Cowan et al. |
| 11,389,585 B2 | 7/2022 | Spohn et al. |

(56) References Cited

U.S. PATENT DOCUMENTS

| | | |
|---|---|---|
| 11,413,403 B2 | 8/2022 | Yoshioka et al. |
| 11,547,793 B2 | 1/2023 | Cowan et al. |
| 11,738,152 B2 | 8/2023 | Haury et al. |
| 2001/0004466 A1 | 6/2001 | Heinz et al. |
| 2001/0018575 A1 | 8/2001 | Lyza |
| 2002/0010596 A1 | 1/2002 | Matory |
| 2002/0147429 A1 | 10/2002 | Cowan et al. |
| 2003/0216695 A1 | 11/2003 | Yang |
| 2003/0226539 A1 | 12/2003 | Kim et al. |
| 2004/0068224 A1 | 4/2004 | Couvillon et al. |
| 2004/0092905 A1 | 5/2004 | Azzolini |
| 2004/0116893 A1 | 6/2004 | Spohn et al. |
| 2004/0154788 A1 | 8/2004 | Symonds |
| 2004/0186457 A1 | 9/2004 | Truitt et al. |
| 2004/0249344 A1 | 12/2004 | Nemoto et al. |
| 2004/0254541 A1 | 12/2004 | Wong et al. |
| 2005/0082828 A1 | 4/2005 | Wicks et al. |
| 2006/0052794 A1 | 3/2006 | Mcgill et al. |
| 2006/0149213 A1 | 7/2006 | Raybuck |
| 2007/0068964 A1 | 3/2007 | Tanaami et al. |
| 2007/0129705 A1 | 6/2007 | Trombley et al. |
| 2008/0045925 A1 | 2/2008 | Stepovich et al. |
| 2008/0146996 A1 | 6/2008 | Smisson et al. |
| 2009/0069792 A1 | 3/2009 | Frey et al. |
| 2009/0112087 A1 | 4/2009 | Fago |
| 2009/0216192 A1 | 8/2009 | Schriver et al. |
| 2009/0218243 A1 | 9/2009 | Gyrn et al. |
| 2010/0063445 A1 | 3/2010 | Sternberg et al. |
| 2010/0089475 A1 | 4/2010 | Tracey |
| 2010/0091361 A1 | 4/2010 | Yuuki |
| 2010/0114064 A1 | 5/2010 | Kalafut et al. |
| 2010/0286650 A1 | 11/2010 | Fitzgerald |
| 2011/0009826 A1 | 1/2011 | Lewis |
| 2011/0218434 A1 | 9/2011 | Ziemba et al. |
| 2011/0275988 A1 | 11/2011 | Davis et al. |
| 2011/0282196 A1 | 11/2011 | Martz |
| 2012/0020911 A1 | 1/2012 | Seliktar et al. |
| 2012/0101472 A1 | 4/2012 | Schroeder et al. |
| 2012/0178629 A1 | 7/2012 | Hudson et al. |
| 2012/0209111 A1 | 8/2012 | Cowan et al. |
| 2012/0217231 A1 | 8/2012 | Moore et al. |
| 2012/0245560 A1 | 9/2012 | Hochman |
| 2012/0253291 A1 | 10/2012 | Ivosevic et al. |
| 2013/0023048 A1 | 1/2013 | Kim et al. |
| 2013/0030291 A1 | 1/2013 | Lewis |
| 2013/0043273 A1 | 2/2013 | Lee et al. |
| 2013/0053774 A1 | 2/2013 | Kirkpatrick |
| 2013/0067416 A1 | 3/2013 | Barron et al. |
| 2013/0204130 A1 | 8/2013 | McArthur et al. |
| 2013/0211248 A1 | 8/2013 | Cowan et al. |
| 2013/0310756 A1 | 11/2013 | Whalley et al. |
| 2014/0124087 A1 | 5/2014 | Anderson et al. |
| 2014/0261713 A1 | 9/2014 | Schriver et al. |
| 2014/0276652 A1 | 9/2014 | Gittard |
| 2014/0374353 A1 | 12/2014 | Wright et al. |
| 2015/0174338 A1 | 6/2015 | Takemoto |
| 2015/0260325 A1 | 9/2015 | Quick |
| 2016/0030662 A1 | 2/2016 | Uber, III et al. |
| 2016/0250409 A1 | 9/2016 | Dedig et al. |
| 2017/0035974 A1 | 2/2017 | Berry et al. |
| 2017/0056604 A1* | 3/2017 | Cowan .................. A61M 5/315 |
| 2017/0100534 A1 | 4/2017 | Fukikoshi et al. |
| 2017/0165427 A1 | 6/2017 | Uber, III et al. |
| 2017/0232173 A1 | 8/2017 | Perry et al. |
| 2018/0161496 A1 | 6/2018 | Berry et al. |
| 2018/0280630 A1 | 10/2018 | Jiang et al. |
| 2018/0296755 A1 | 10/2018 | Dahlin et al. |
| 2018/0318507 A1* | 11/2018 | Cowan ................ A61M 5/5086 |
| 2018/0339146 A1* | 11/2018 | Schrauder ............. A61M 5/281 |
| 2018/0344935 A1* | 12/2018 | Mcdermott ........... A61M 5/007 |
| 2019/0192770 A1* | 6/2019 | Spohn ............... A61M 5/14546 |
| 2020/0164141 A1 | 5/2020 | Biermann et al. |
| 2020/0206490 A1 | 7/2020 | Bae |
| 2020/0246541 A1 | 8/2020 | Neftel et al. |
| 2021/0023298 A1 | 1/2021 | McDermott et al. |
| 2021/0146064 A1* | 5/2021 | Knutsson ............ A61M 5/5013 |
| 2021/0193289 A1 | 6/2021 | Cowan et al. |
| 2021/0220561 A1 | 7/2021 | Spohn et al. |
| 2021/0316065 A1 | 10/2021 | Berry et al. |
| 2021/0353870 A1 | 11/2021 | Volkar et al. |
| 2023/0146744 A1 | 5/2023 | Cowan et al. |
| 2023/0181816 A1 | 6/2023 | Lee |

FOREIGN PATENT DOCUMENTS

| | | |
|---|---|---|
| EP | 0446898 A2 | 9/1991 |
| EP | 1086661 A2 | 3/2001 |
| EP | 1572266 A2 | 9/2005 |
| EP | 1769849 A1 | 4/2007 |
| EP | 1800704 A1 | 6/2007 |
| EP | 2005934 A2 | 12/2008 |
| EP | 2098258 A1 | 9/2009 |
| EP | 2692375 A1 | 2/2014 |
| EP | 2719420 A1 | 4/2014 |
| EP | 2754459 A1 | 7/2014 |
| EP | 2767299 A1 | 8/2014 |
| EP | 3057648 A1 | 8/2016 |
| EP | 2962770 B1 | 3/2017 |
| EP | 3248635 A1 | 11/2017 |
| FR | 1288915 A | 3/1962 |
| GB | 1173662 A | 12/1969 |
| GB | 2214819 A | 9/1989 |
| GB | 2374143 A | 10/2002 |
| JP | H02-88664 | 7/1990 |
| JP | H0849598 A | 2/1996 |
| JP | H10999034 A | 4/1997 |
| JP | 5485885 B2 | 5/2014 |
| JP | 5511409 B2 | 6/2014 |
| JP | 5882595 B2 | 3/2016 |
| JP | 5897798 B2 | 3/2016 |
| JP | 6552258 B2 | 7/2019 |
| JP | 6839853 B2 | 3/2021 |
| KR | 100985378 B1 | 10/2010 |
| WO | 9221391 A1 | 12/1992 |
| WO | 9528195 A1 | 10/1995 |
| WO | 9707841 A2 | 3/1997 |
| WO | 0204049 A1 | 1/2002 |
| WO | 02066100 A2 | 8/2002 |
| WO | 2004033023 A1 | 4/2004 |
| WO | 2005035995 A1 | 4/2005 |
| WO | 2007133942 A2 | 11/2007 |
| WO | 2008050218 A2 | 5/2008 |
| WO | 2008153831 A2 | 12/2008 |
| WO | 2009038955 A1 | 3/2009 |
| WO | 2010004206 A2 | 1/2010 |
| WO | 2010014654 A1 | 2/2010 |
| WO | 2011011346 A1 | 1/2011 |
| WO | 2011125303 A1 | 10/2011 |
| WO | 2011129175 A1 | 10/2011 |
| WO | 2012061140 A1 | 5/2012 |
| WO | 2012155035 A1 | 11/2012 |
| WO | 2013043868 A1 | 3/2013 |
| WO | 2013043881 A1 | 3/2013 |
| WO | 2013043889 A1 | 3/2013 |
| WO | 2014027009 A1 | 2/2014 |
| WO | 2014055283 A1 | 4/2014 |
| WO | 2014160326 A1 | 10/2014 |
| WO | 2015058088 A1 | 4/2015 |
| WO | 2015066506 A2 | 5/2015 |
| WO | 2015164783 A1 | 10/2015 |
| WO | 2016058946 A1 | 4/2016 |
| WO | 2016069711 A1 | 5/2016 |
| WO | 2016069714 A1 | 5/2016 |
| WO | 2016112163 A1 | 7/2016 |
| WO | 2016157886 A1 | 10/2016 |
| WO | 2016172467 A1 | 10/2016 |
| WO | 2016190904 A1 | 12/2016 |
| WO | 2016191485 A1 | 12/2016 |
| WO | 2017040154 A1 | 3/2017 |
| WO | 2017091635 A1 | 6/2017 |
| WO | 2017091636 A1 | 6/2017 |
| WO | 2017091643 A1 | 6/2017 |
| WO | 2018053074 A1 | 3/2018 |
| WO | 2018057386 A1 | 3/2018 |

(56) References Cited

FOREIGN PATENT DOCUMENTS

| | | | |
|---|---|---|---|
| WO | 2018218132 A1 | 11/2018 |
| WO | 2019046259 A1 | 3/2019 |
| WO | 2019046260 A1 | 3/2019 |
| WO | 2019046299 A1 | 3/2019 |
| WO | 2019152978 A1 | 8/2019 |
| WO | 2019204605 A1 | 10/2019 |
| WO | 2019204617 A1 | 10/2019 |
| WO | 2020055785 A1 | 3/2020 |
| WO | 2020055818 A1 | 3/2020 |
| WO | 2021050507 A1 | 3/2021 |
| WO | 2021168076 A1 | 8/2021 |
| WO | 2021173743 A1 | 9/2021 |
| WO | 2021188416 A1 | 9/2021 |
| WO | 2021188460 A1 | 9/2021 |
| WO | 2021222619 A1 | 11/2021 |
| WO | 2021247595 A1 | 12/2021 |
| WO | 2021257667 A1 | 12/2021 |
| WO | 2021257699 A1 | 12/2021 |
| WO | 2022035791 A1 | 2/2022 |
| WO | 2022036058 A1 | 2/2022 |
| WO | 2022265695 A1 | 12/2022 |

OTHER PUBLICATIONS

International Preliminary Report on Patentability from PCT Application No. PCT/US2021/045298, Feb. 23, 2023.
UN Haluk, A New Device Preventing Air Embolism During The Angiography, Air Trap Device: An In-Vitro Experimental Air Emboli Study, Proceedings of the 2019 Design of Medical Devices Conference, 2019.

\* cited by examiner

FEATURES FOR ANGIOGRAPHY SYRINGE

CROSS REFERENCE TO RELATED APPLICATIONS

This application is a U.S. national phase application under 35 U.S.C. § 371 of PCT International Application No. PCT/US2021/045298, filed Aug. 10, 2021, and claims the benefit of U.S. Provisional Patent Application No. 62/706,340, filed on Aug. 11, 2020, and U.S. Provisional Patent Application No. 63/073,519, filed on Sep. 2, 2020, the disclosures of which are incorporated by reference in their entireties.

BACKGROUND

Field of the Technology

The present disclosure is related generally to features associated with an angiography syringe. The described features provide strength to the distal end, help prevent fluid spillage from the tip, improve ease of use, and improve visualization processes.

Background

Syringe injection systems are among the medical devices used in medical imaging procedures for many years. Many such syringes are operated manually by advancing a plunger extension in operative connection with an internal plunger to pressurize the fluid within the syringe. In numerous medical injection procedures, however, accurate control and/or high pressures may be employed that cannot be achieved via manual syringe operation. A number of syringes and powered injectors for use therewith have, therefore, been developed for use in medical procedures such as angiography (CV), computed tomography (CT) and nuclear magnetic resonance (NMR)/magnetic resonance imaging (MRI). For example, U.S. Pat. No. 5,383,858 discloses a front-loading syringe and powered injector in both pressure jacket and jacketless configurations, the disclosure of which is incorporated herein by reference.

In certain fluid injectors, such as high pressure fluid injectors including pressure jackets to surround the body of the syringe to prevent syringe expansion and/or failure under the high injection pressures, mounting the syringe on the fluid injector may include multiple steps to correctly engage the syringe with the fluid injector and pressure jacket. For example, some pressure jackets cover large portions of the distal end of the syringe to prevent failure of the distal end under high injection pressures. This may complicate loading of the syringe into the pressure jacket and subsequent engagement with the fluid injector. Similarly, the presence of the pressure jacket around the barrel and distal end of the syringe may make visualization of the syringe and contents difficult, for example ensuring that a liquid has been loaded into a syringe and that no air bubbles are present in the liquid.

Once the syringe is engaged with the fluid injector, to load syringes with contrast fluid or saline, a user typically connects a fill tube or spike to the front nozzle or discharge outlet of the syringe and places the other end of the tube/spike in fluid communication with a bottle or bag of contrast medium, saline, or other fluid. The plunger of the syringe is retracted (usually by means of an injector piston) to aspirate the fluid into the syringe until the desired amount is loaded into the syringe. After the syringe is filled, the fill tube is removed from the syringe tip. Often, small amounts of contrast or other fluid, such as saline, contained in the fill tube may drip therefrom onto the floor or injector. Fluid drips may also occur in multi-patient set-ups, where a first portion of the syringes and tubing may be used over multiple injection procedures and a second portion may be discarded after a single use and replace with a new single-use portion before a subsequent injection procedure. Such fluid drips may contaminate and foul various injector components, drip on the floor creating a hazard for the technician and patient, and/or contaminate various surfaces within the fluid injection suite and should be minimized and avoided.

After the syringe is filled with fluid, a connector tube or priming tube is connected to the discharge outlet of the syringe and the syringe and connector tube are primed (typically by advancing the plunger in the syringe) to eject air from the syringe and the connector tube (i.e., to prevent air from being injected into the patient). While this technique may be effective in purging air from the tubing connected to the syringe, it is undesirable to have fluids dispensed from the end of the tube. Often, the fluids dispensed from the end of the tube foul the exterior surface of the tubing, syringe, and/or injector, drip, or leak from the various connections and fall onto the floor. When dealing with contrast media, this is particularly undesirable because the media is very sticky and tends to migrate to whatever surface the operator touches after purging the tube.

Furthermore, in some applications a direct vented spike is positioned on top of a syringe. The vented spike is used to pierce a bottle of contrast fluid or saline fluid to be delivered to the patient. In such applications, when the bottle and the spike is removed from the syringe, the fluid remaining in the spike can drip out onto the syringe tip.

Syringes for use in contrast enhanced imaging procedures that are easily engaged with the injector, allow ready viewing and characterization of the syringe fill state, and reduce the effects of contrast fouling and fluid drippage and enhanced features are desired.

SUMMARY

The present disclosure provides a syringe suitable for use in powered fluid injections in contrast enhanced imaging procedures, such as computed tomography (CT), angiography (CV), and magnetic resonance imaging (MRI) that includes features that reduce the impact of fluid drips and further include other features that improve the syringe capabilities, as described herein.

According to one exemplary and non-limiting embodiment, a syringe may include a proximal end, a distal end, and a cylindrical sidewall extending between the proximal end and the distal end, wherein the distal end comprises a conical distal end wall and a fluid nozzle at a distal end of the conical distal end wall; a cylindrical load bearing wall extending axially from the cylindrical sidewall past a proximal end of the conical distal end wall; and a plurality of radial ribs positioned around a periphery of the conical distal end wall, wherein a longitudinal axis of the plurality of radial ribs extends radially inward from the cylindrical load bearing wall towards the fluid nozzle over at least a portion of the conical distal end wall.

According to one exemplary and non-limiting embodiment, the plurality of radial ribs may define plurality of fluid retention channels between each pair of adjacent radial ribs, wherein the plurality of fluid retention channels is configured to retain a volume of liquid by capillary adhesion when the syringe is rotated from a first upward facing position to a second downward facing position. The plurality of fluid retention channels may be configured to retain a volume of the liquid ranging from 0.1 to 0.8 milliliters. A volume of the liquid that the plurality of fluid retention channels holds may be at least partially determined from a distance between each adjacent pair of the plurality of radial ribs, a height of each adjacent pair of the plurality of radial ribs, and a distance that each pair of radial ribs distally extend radially inward from the conical distal end wall. The plurality of radial ribs may increase a load strength of the conical distal end wall. The plurality of radial ribs may increase a load strength of the cylindrical load bearing wall. At least one of the plurality of radial ribs may extend a different radial distance inward from the cylindrical load bearing wall over the conical distal end wall than the remaining radial ribs of the plurality of radial ribs. The cylindrical load bearing wall may be configured to abut a retaining surface of a retaining arm of a fluid injector to retain the syringe within a pressure jacket during a pressurized injection procedure. The cylindrical load bearing wall may extend axially from the cylindrical sidewall of the syringe at an angle of from 1 degree to 30 degrees relative to a longitudinal axis of the syringe. A distal surface of the cylindrical load bearing wall may be angled radially from a more proximal inner portion to a more distal outer portion relative to the longitudinal axis of the syringe. The angle of the distal surface of the cylindrical load bearing wall may be configured to prevent entry of fluid between the cylindrical sidewall of the syringe and a pressure jacket in which the syringe is placed. The angle of the distal surface of the cylindrical load bearing wall may be configured to increase a radially inward force on the retaining arm of the fluid injector. At least one of the cylindrical load bearing wall and the plurality of radial ribs may enhance a refraction halo effect at a distal portion of the conical distal end wall of electromagnetic radiation emitted from at least one electromagnetic radiation source in a piston or plunger head of a fluid injector. A neck may be associated with the fluid nozzle at the distal end of the syringe, the neck including a fluid passageway having a plurality of fluid diverting ribs extending radially inward at least partially into the fluid passageway from an inner surface of the neck. The plurality of fluid diverting ribs may be configured to divert a fluid flowing through the neck into the syringe so that the fluid flows along an internal surface of the conical distal end wall and the cylindrical sidewall of the syringe. The plurality of fluid diverting ribs may be configured to minimize an amount of air bubbles in the fluid in the syringe. The amount of air bubbles in the fluid in the syringe may be minimized by the fluid flowing along the internal surface of the distal end wall and the cylindrical sidewall of the syringe. At least a portion of the plurality of fluid diverting ribs may have different profiles. At least a portion of the plurality of flow diverting ribs may extend from the inner surface at different distances into the fluid passageway. The plurality of radial ribs may extend along the conical distal end wall at an angle relative to a longitudinal axis of the syringe such that a distance between each adjacent pair of the plurality of radial ribs tapers from the cylindrical load bearing wall to the fluid nozzle.

According to one exemplary and non-limiting embodiment, a syringe may include a proximal end, a distal end, and a cylindrical sidewall extending between the proximal end and the distal end, wherein the distal end comprises a conical distal end wall and a fluid nozzle at a distal end of the conical distal end wall; a plurality of fluid diverting ribs extending inwardly from an inner surface of the fluid nozzle; and a plurality of radial ribs positioned around a periphery of the conical distal end wall, wherein a longitudinal axis of the plurality of radial ribs extends radially inward from the cylindrical load bearing wall towards the fluid nozzle over at least a portion of the conical distal end wall.

According to one exemplary and non-limiting embodiment, a cylindrical load bearing wall may extend axially from the cylindrical sidewall past a proximal end of the conical distal end wall. The plurality of radial ribs may define a plurality of fluid retention channels between each pair of adjacent radial ribs, wherein the plurality of fluid retention channels is configured to retain a volume of liquid by capillary adhesion when the syringe is rotated from a first upward facing position to a second downward facing position. The plurality of fluid retention channels may be configured to retain a volume of the liquid ranging from 0.1 to 0.8 milliliters. A volume of the liquid that the plurality of fluid retention channels holds may be at least partially determined from a distance between each adjacent pair of the plurality of radial ribs, a height of each adjacent pair of the plurality of radial ribs, and a distance that each pair of radial ribs distally extend radially inward from the conical distal end wall.

According to one exemplary and non-limiting embodiment, a syringe may include a proximal end, a distal end, and a cylindrical sidewall extending between the proximal end and the distal end, wherein the distal end comprises a conical distal end wall and a fluid nozzle at a distal end of the conical distal end wall; and a plurality of fluid diverting ribs extending inwardly from an inner surface of the fluid nozzle, wherein the plurality of fluid diverting ribs enhances a refraction halo effect at a distal portion of the conical distal end wall of electromagnetic radiation emitted from at least one electromagnetic radiation source in a piston or plunger head of a fluid injector.

According to one exemplary and non-limiting embodiment, a cylindrical load bearing wall may extend axially from the cylindrical sidewall past a proximal end of the conical distal end wall. A plurality of radial ribs may be positioned around a periphery of the conical distal end wall, wherein a longitudinal axis of the plurality of radial ribs extends radially inward from the cylindrical load bearing wall towards the fluid nozzle over at least a portion of the conical distal end wall. The plurality of radial ribs may define a plurality of fluid retention channels between each pair of adjacent radial ribs, wherein the plurality of fluid retention channels is configured to retain a volume of liquid by capillary adhesion when the syringe is rotated from a first upward facing position to a second downward facing position. The plurality of fluid retention channels may be configured to retain a volume of the liquid ranging from 0.1 to 0.8 milliliters. A volume of the liquid that the plurality of fluid retention channels holds may be at least partially determined from a distance between each adjacent pair of the plurality of radial ribs, a height of each adjacent pair of the plurality of radial ribs, and a distance that each pair of radial ribs distally extend radially inward from the conical distal end wall.

In one aspect, a syringe with improved features is provided according to the following clauses.

Clause 1: A syringe comprising: a proximal end, a distal end, and a cylindrical sidewall extending between the proximal end and the distal end, wherein the distal end comprises a conical distal end wall and a fluid nozzle at a distal end of the conical distal end wall; a cylindrical load bearing wall extending axially from the cylindrical sidewall past a proximal end of the conical distal end wall; and a plurality of radial ribs positioned around a periphery of the conical distal end wall, wherein a longitudinal axis of the plurality of radial ribs extends radially inward from the cylindrical load bearing wall towards the fluid nozzle over at least a portion of the conical distal end wall.

Clause 2: The syringe of Clause 1, wherein the plurality of radial ribs defines plurality of fluid retention channels between each pair of adjacent radial ribs, wherein the plurality of fluid retention channels is configured to retain a volume of liquid by capillary adhesion when the syringe is rotated from a first upward facing position to a second downward facing position.

Clause 3: The syringe of Clause 2, wherein the plurality of fluid retention channels are configured to retain a volume of the liquid ranging from 0.1 to 0.8 milliliters.

Clause 4: The syringe of Clause 2, wherein a volume of the liquid that the plurality of fluid retention channels holds is at least partially determined from a distance between each adjacent pair of the plurality of radial ribs, a height of each adjacent pair of the plurality of radial ribs, and a distance that each pair of radial ribs distally extend radially inward from the conical distal end wall.

Clause 5: The syringe of any of Clauses 1 to 4, wherein the plurality of radial ribs increases a load strength of the conical distal end wall.

Clause 6: The syringe of any of Clauses 1 to 5, wherein the plurality of radial ribs increases a load strength of the cylindrical load bearing wall.

Clause 7: The syringe of any of Clauses 1 to 6, wherein at least one of the plurality of radial ribs extends a different radial distance inward from the cylindrical load bearing wall over the conical distal end wall than the remaining radial ribs of the plurality of radial ribs.

Clause 8: The syringe of any of Clauses 1 to 7, wherein the cylindrical load bearing wall is configured to abut a retaining surface of a retaining arm of a fluid injector to retain the syringe within a pressure jacket during a pressurized injection procedure.

Clause 9: The syringe of any of Clauses 1 to 8, wherein the cylindrical load bearing wall extends axially from the cylindrical sidewall of the syringe at an angle of from 1 degree to 30 degrees relative to a longitudinal axis of the syringe.

Clause 10: The syringe of any of Clauses 1 to 9, wherein a distal surface of the cylindrical load bearing wall is angled radially from a more proximal inner portion to a more distal outer portion relative to the longitudinal axis of the syringe.

Clause 11: The syringe of Clause 10, wherein the angle of the distal surface of the cylindrical load bearing wall is configured to prevent entry of fluid between the cylindrical sidewall of the syringe and a pressure jacket in which the syringe is placed.

Clause 12: The syringe of Clause 10 or Clause 11, wherein the angle of the distal surface of the cylindrical load bearing wall is configured to increase a radially inward force on the retaining arm of the fluid injector.

Clause 13: The syringe of any of Clauses 1 to 12, wherein at least one of the cylindrical load bearing wall and the plurality of radial ribs enhances a refraction halo effect at a distal portion of the conical distal end wall of electromagnetic radiation emitted from at least one electromagnetic radiation source in a piston or plunger head of a fluid injector.

Clause 14: The syringe of any of Clauses 1 to 13, further comprising a neck associated with the fluid nozzle at the distal end of the syringe, the neck including a fluid passageway having a plurality of fluid diverting ribs extending radially inward at least partially into the fluid passageway from an inner surface of the neck.

Clause 15: The syringe of Clause 14, wherein the plurality of fluid diverting ribs are configured to divert a fluid flowing through the neck into the syringe so that the fluid flows along an internal surface of the conical distal end wall and the cylindrical sidewall of the syringe.

Clause 16: The syringe of Clause 14 or Clause 15, wherein the plurality of fluid diverting ribs are configured to minimize an amount of air bubbles in the fluid in the syringe.

Clause 17: The syringe of Clause 16, wherein the amount of air bubbles in the fluid in the syringe is minimized by the fluid flowing along the internal surface of the distal end wall and the cylindrical sidewall of the syringe.

Clause 18: The syringe of any of Clauses 14 to 17, wherein at least a portion of the plurality of fluid diverting ribs have different profiles.

Clause 19: The syringe of any of Clauses 14 to 18, wherein at least a portion of the plurality of flow diverting ribs extend from the inner surface at different distances into the fluid passageway.

Clause 20: The syringe of any of Clauses 1 to 19, wherein the plurality of radial ribs extend along the conical distal end wall at an angle relative to a longitudinal axis of the syringe such that a distance between the each adjacent pair of the plurality of radial ribs tapers from the cylindrical load bearing wall to the fluid nozzle.

Clause 21: A syringe comprising: a proximal end, a distal end, and a cylindrical sidewall extending between the proximal end and the distal end, wherein the distal end comprises a conical distal end wall and a fluid nozzle at a distal end of the conical distal end wall; a plurality of fluid diverting ribs extending inwardly from an inner surface of the fluid nozzle; and a plurality of radial ribs positioned around a periphery of the conical distal end wall, wherein a longitudinal axis of the plurality of radial ribs extends radially inward from the cylindrical load bearing wall towards the fluid nozzle over at least a portion of the conical distal end wall.

Clause 22: The syringe of Clause 21, further comprising a cylindrical load bearing wall extending axially from the cylindrical sidewall past a proximal end of the conical distal end wall.

Clause 23: The syringe of Clause 21 or Clause 22, wherein the plurality of radial ribs defines plurality of fluid retention channels between each pair of adjacent radial ribs, wherein the plurality of fluid retention channels is configured to retain a volume of liquid by capillary adhesion when the syringe is rotated from a first upward facing position to a second downward facing position.

Clause 24: The syringe of Clause 23, wherein the plurality of fluid retention channels are configured to retain a volume of the liquid ranging from 0.1 to 0.8 milliliters.

Clause 25: The syringe of Clause 23, wherein a volume of the liquid that the plurality of fluid retention channels holds is at least partially determined from a distance between each adjacent pair of the plurality of radial ribs, a height of each adjacent pair of the plurality of radial ribs, and a distance that each pair of radial ribs distally extend radially inward from the conical distal end wall.

Clause 26: A syringe comprising: a proximal end, a distal end, and a cylindrical sidewall extending between the proximal end and the distal end, wherein the distal end comprises a conical distal end wall and a fluid nozzle at a distal end of the conical distal end wall; and a plurality of fluid diverting ribs extending inwardly from an inner surface of the fluid nozzle, wherein the plurality of fluid diverting ribs enhances a refraction halo effect at a distal portion of the conical distal end wall of electromagnetic radiation emitted from at least one electromagnetic radiation source in a piston or plunger head of a fluid injector.

Clause 27: The syringe of Clause 26, further comprising a cylindrical load bearing wall extending axially from the cylindrical sidewall past a proximal end of the conical distal end wall.

Clause 28: The syringe of Clause 26 or Clause 27, further comprising a plurality of radial ribs positioned around a periphery of the conical distal end wall, wherein a longitudinal axis of the plurality of radial ribs extends radially inward from the cylindrical load bearing wall towards the fluid nozzle over at least a portion of the conical distal end wall.

Clause 29: The syringe of Clause 28, wherein the plurality of radial ribs defines plurality of fluid retention channels between each pair of adjacent radial ribs, wherein the plurality of fluid retention channels is configured to retain a volume of liquid by capillary adhesion when the syringe is rotated from a first upward facing position to a second downward facing position.

Clause 30: The syringe of Clause 29, wherein the plurality of fluid retention channels are configured to retain a volume of the liquid ranging from 0.1 to 0.8 milliliters.

Clause 31: The syringe of Clause 29, wherein a volume of the liquid that the plurality of fluid retention channels holds is at least partially determined from a distance between each adjacent pair of the plurality of radial ribs, a height of each adjacent pair of the plurality of radial ribs, and a distance that each pair of radial ribs distally extend radially inward from the conical distal end wall.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices, and/or processes, and/or other subject matter described herein will become apparent in the teachings set forth herein. In addition to the illustrative aspects and features described above, further aspects and features will become apparent by reference to the drawings and the following detailed description.

BRIEF DESCRIPTION OF THE DRAWINGS

The novel features described herein are set forth with particularity in the appended claims. Such features, however, both as to organization and methods of operation may be better understood by reference to the following description, taken in conjunction with the accompanying drawings.

DETAILED DESCRIPTION

Figure 1:
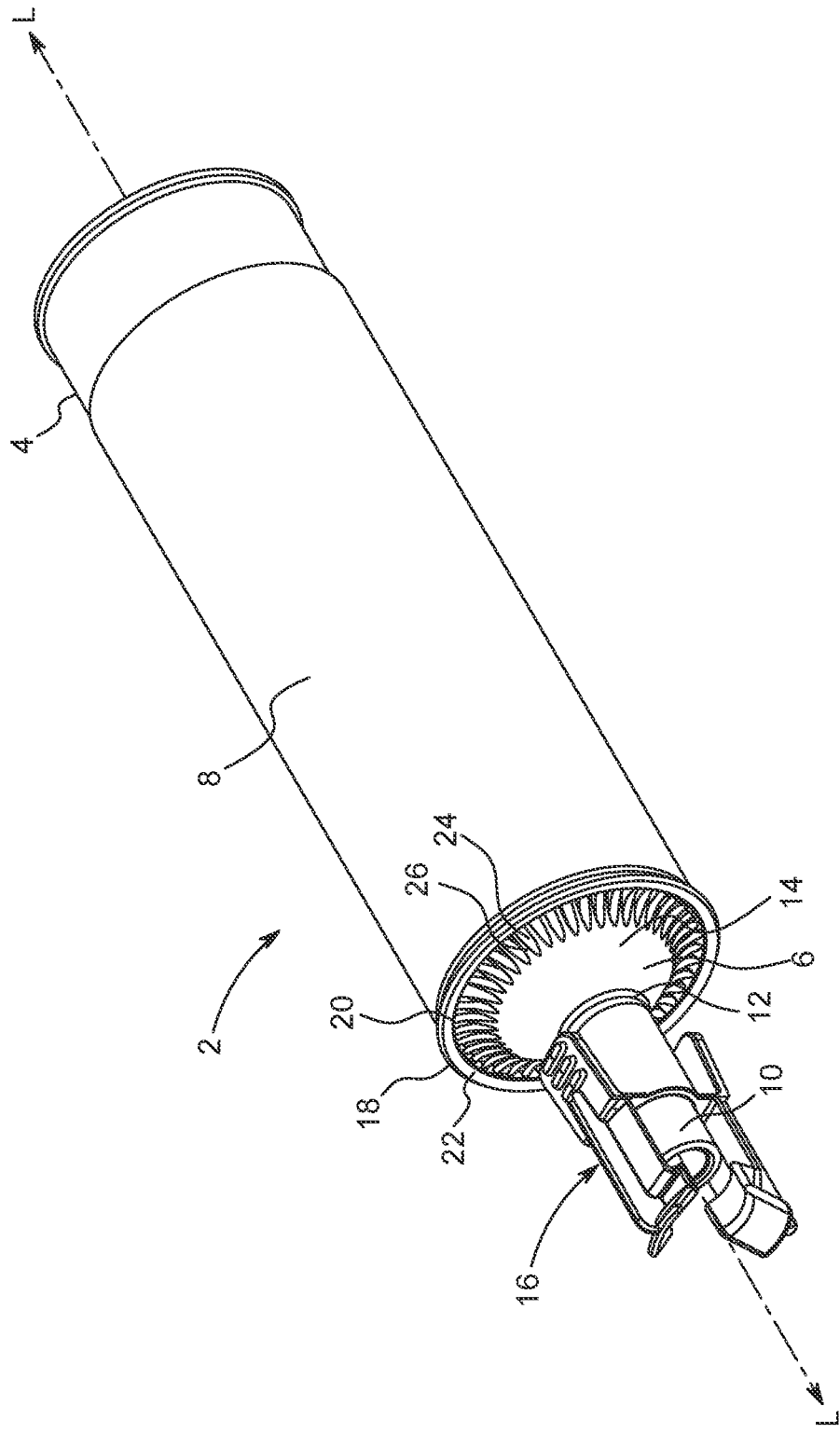
FIG. 1 is a perspective view of a syringe according to one example of the present disclosure.

In the following detailed description, reference is made to the accompanying drawings, which form a part hereof. The illustrative features shown and described in the detailed description, drawings, and claims are not meant to be limiting. Other features may be utilized, and other changes may be made, without departing from the scope of the subject matter presented here.

Before explaining the various aspects of the syringe assembly and various features thereof in detail, it should be noted that the various aspects disclosed herein are not limited in their application or use to the details of construction and arrangement of parts illustrated in the accompanying drawings and description. Rather, the disclosed devices may be positioned or incorporated in other devices, variations, and modifications thereof, and may be practiced or carried out in various ways. Accordingly, aspects of the syringe and syringe features disclosed herein are illustrative in nature and are not meant to limit the scope or application thereof. Furthermore, unless otherwise indicated, the terms and expressions employed herein have been chosen for the purpose of describing the various aspects of the syringe and syringe features for the convenience of the reader and are not to limit the scope thereof. In addition, it should be understood that any one or more of the components of the syringe and syringe features, expressions thereof, and/or examples thereof, can be combined with any one or more of the other components, expressions thereof, and/or examples thereof, without limitation.

Also, in the following description, it is to be understood that terms such as front, back, inside, outside, top, bottom and the like are words of convenience and are not to be construed as limiting terms. As used herein, the term "proximal" when used to describe a portion of a syringe is generally used to indicate the portion of the syringe closer to the injector and the term "distal" when used to describe a portion of a syringe is generally used to indicate the portion of the syringe closer to the patient (i.e., the nozzle end of the syringe). Terminology used herein is not meant to be limiting insofar as devices described herein, or portions thereof, may be attached or utilized in other orientations. The various aspects of the syringe and syringe features will be described in more detail with reference to the drawings.

The present disclosure is drawn to a syringe design for use with a powered fluid injector used in medical imaging procedures. According to various embodiments, certain medical imaging procedures may include injection of a contrast media or agent that highlights certain features in the medical image. Known as contrast enhanced medical imaging, the process generally involves injection of a contrast media with a suitable flushing agent, such as saline, prior to or during the imaging process. Powered fluid injectors have been used to control injection of the fluids and are typically designed with one or more syringes for holding and dispensing the contrast media, the flushing fluid, and other medical fluids administered prior to or during the imaging procedure. For example, U.S. Pat. Nos. 5,383,858; 6,652,489; 7,563,249; 8,945,051; 9,173,995; and 10,507,319 disclose front-loading syringes and powered injectors in pressure jacket and jacketless examples, the disclosure is incorporated by this reference. Common contrast enhanced medical imaging procedures include computed tomography (CT), magnetic resonance imaging (MRI), positron emission tomography (PET, SPECT), and angiography (CV). Due to the viscosity and need to deliver volumes of contrast during a short period of time through small diameter tubing sets and/or catheters, to provide a "tight bolus," certain injection procedures may be performed at high injection pressures, such as pressures up to 300 psi for CT and MRI, and pressures up to 1200 psi for CV procedures. The injector may be configured to inject or dispense the fluid medium contained in the first, second, and/or further syringes in a controlled manner, such as may be employed in medical procedures such as angiography, CT, PET, and NMR/MRI.

During the injection process, many potential issues may occur that should or must be avoided, for example, difficult or slow loading of the syringe into the pressure jacket, deformation or failure of the syringe or disengaging of syringe from fluid injector due to high injection pressures, dripping of contrast or saline that may foul one or more surfaces on the syringe or injector components, intake of air into the syringe and potential injection of air into the patient, slow fill rates with bubble formation, inability to view syringe contents, among other problems. The presently described syringe and features mitigate or prevent one or more of these issues.

Figure 2:
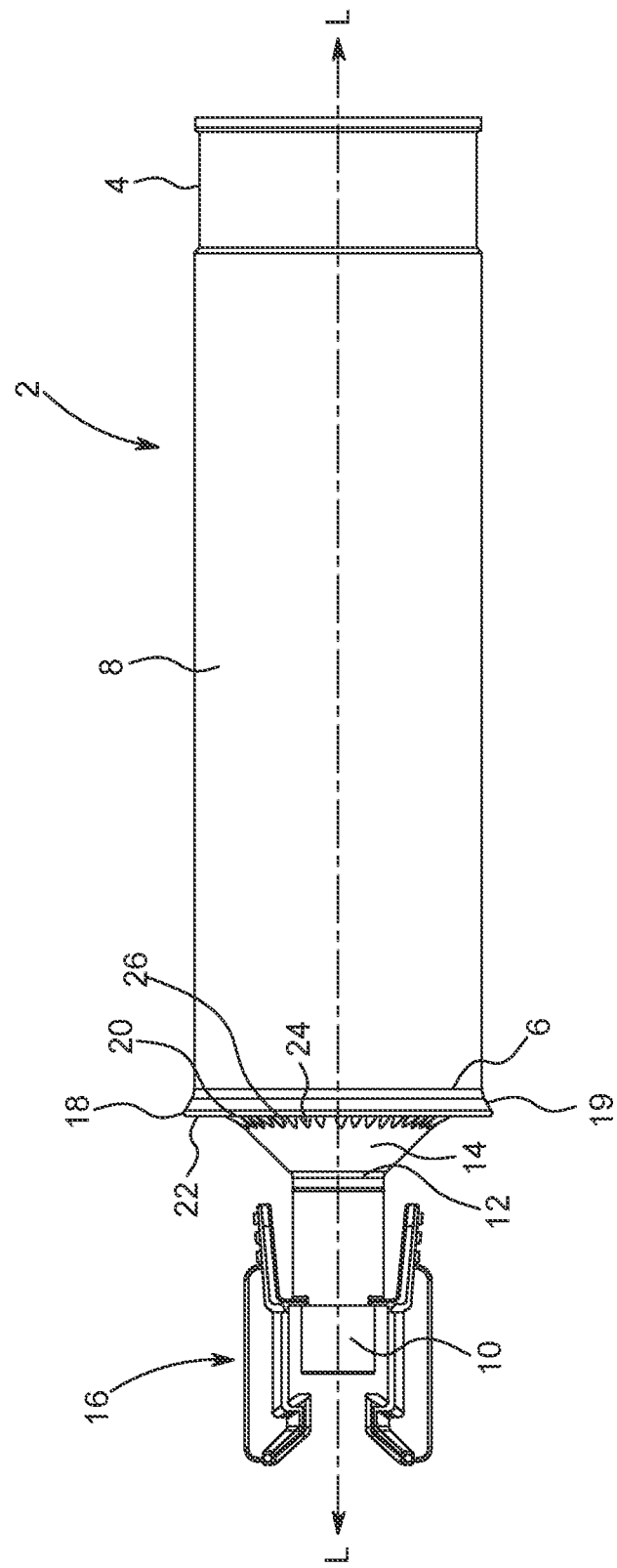
FIG. 2 is a side view of the syringe of FIG. 1.
Figure 3:
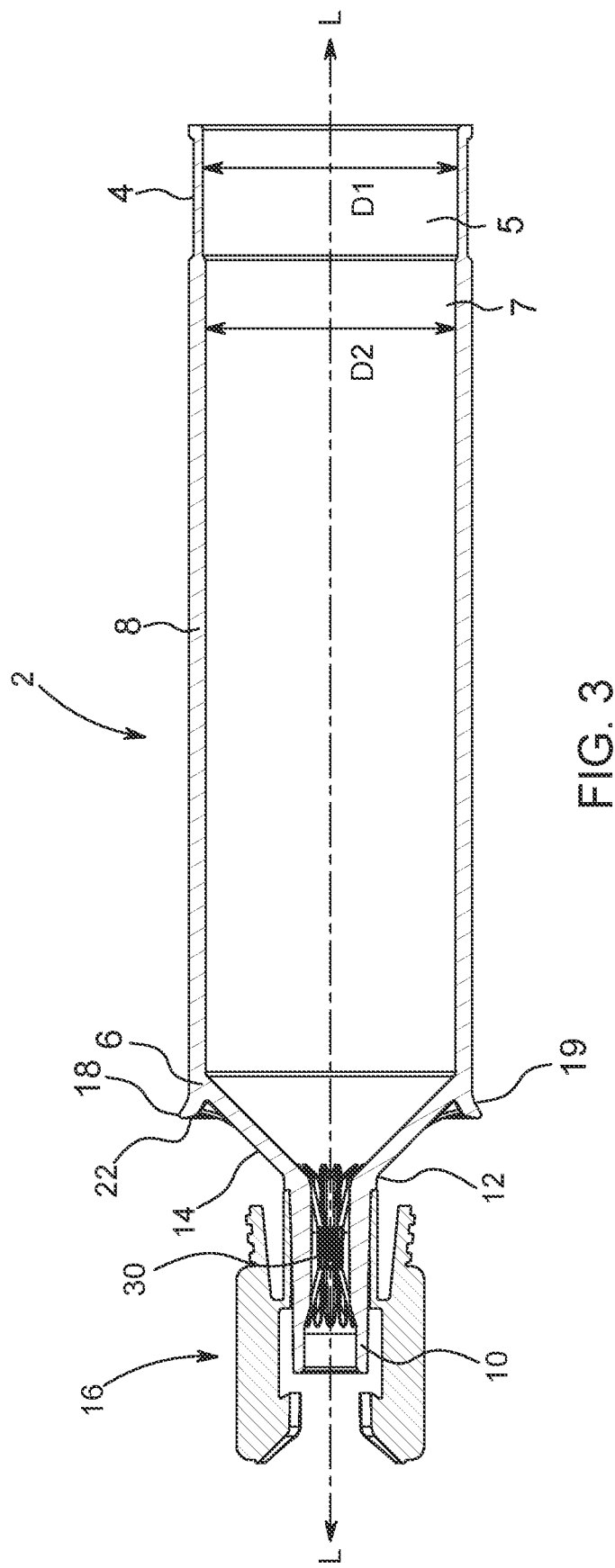
FIG. 3 is a cross-sectional view of the syringe of FIG. 1 along line A-A.

According to a first embodiment, the present disclosure provides a syringe 2 that may include a proximal end 4, a distal end 6, and a cylindrical sidewall 8 extending between the proximal end 4 and the distal end 6. The distal end 6 may include a fluid nozzle 10 at the distal end 12 of a conical distal end wall 14, as shown in FIGS. 1-3. In various embodiments of the present disclosure, the syringe 2 may include an embodiment of a tubing or spike clip 16 as described in International PCT Application No. PCT/US2021/018523, the disclosure of which is incorporated in its entirety by this reference. In other embodiments, the syringe may include a luer-type connector (not shown) or other connector mechanism for connecting the syringe to a tubing set and/or spike.

According to certain embodiments, the syringe 2 may include a cylindrical load bearing wall 18 extending from the cylindrical sidewall 8 distally past a proximal end 20 of the conical distal wall 14. The cylindrical load bearing wall 18 may protrude along a longitudinal axis L and provides a distal surface 22 configured to abut an inner proximal surface 100 of one or more retaining elements 102 at a distal end of one or more retaining arms 103 (see FIGS. 7A and 7B) to retain the syringe 2 within the pressure jacket, keep the syringe 2 engaged with the fluid injector, and bear a load associated by a pressurized fluid delivery (e.g., a load produced by a motor of the fluid injector as it pressurizes the fluid using a motorized piston). For example, in a CT injection protocol, the cylindrical load bearing wall 18 may be configured to bear a load of at least 300 psi. According to other embodiments during a CV injection protocol, the cylindrical load bearing wall 18 may be configured to bear a load associated with the high pressures of an angiography injection. For example, in certain angiography injections, the fluid within the syringe 2 may be pressurized up to 1200 psi. The high pressures may be necessary to deliver the viscous contrast agent or less viscous saline solution through a small diameter catheter typically associated with a CV injection procedure. As the cylindrical load bearing wall 18 abuts the inner wall of the distal end of the pressure jacket, the load from the syringe 2 is transferred to the one or more retaining elements 102 at a distal end of one or more retaining arms 103 and ultimately to frame features of the fluid injector. The cylindrical load bearing wall 18 may be continuous or discontinuous around the circumference of the distal end 6 of the syringe 2. In certain embodiments, the cylindrical load bearing wall 18 is continuous around the circumference of the distal end 6 of the syringe 2.

Figure 7A:
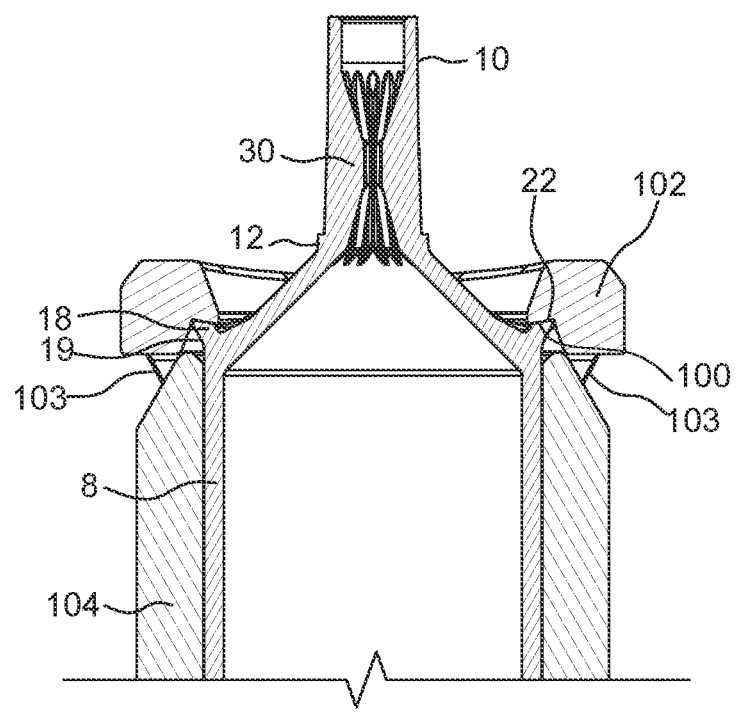
FIG. 7A is a cross-sectional view of a syringe held in a retaining arrangement according to one example of the present disclosure.
Figure 7B:
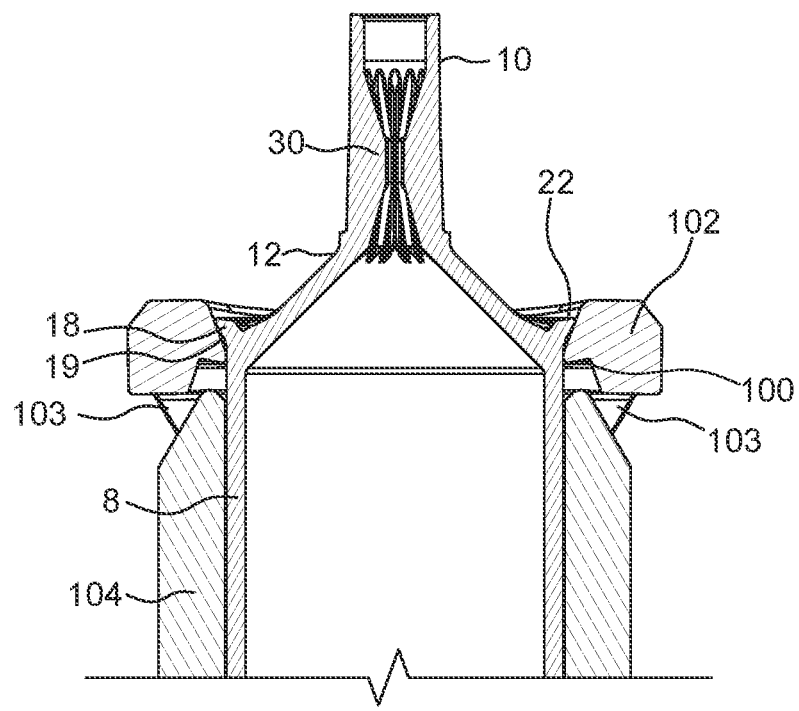
FIG. 7B is a cross-sectional view of the syringe of FIG. 7A being inserted into the retaining arrangement.

In certain embodiments, as shown in FIGS. 2 and 3, the cylindrical load bearing wall 18 extends from and flares out from the cylindrical sidewall 8 toward the distal end, such that the distal outer diameter of the load bearing wall 18 is greater than the outer diameter of the cylindrical sidewall 8. According to certain embodiments, the cylindrical load bearing wall 18 may flare out at an angle of from 1° to 30° relative to the longitudinal axis L of the syringe 2. The flared cylindrical load bearing wall 18 may allow ready installation of the syringe 2 into the pressure jacket 104 and engagement of the syringe 2 and corresponding plunger with the piston of the fluid injector. To be clear, the flared surface 19 flares from the outer surface of the cylindrical sidewall 8 up to the distal surface 22 of the load bearing wall 18. For example, as illustrated in FIGS. 7A and 7B, as the syringe is lowered into the pressure jacket past the one or more retaining elements 102, the flared cylindrical load bearing wall 18 may push the one or more retaining elements 102 and corresponding retaining arms 103 outward. A user may have to apply a certain amount of downward force (for example, the fluid injector and pressure jacket assembly may be in the vertical position with the open end of the pressure jackets pointing vertically upwards) to allow the downward force to move the one or more retaining elements 102 outwards against a biasing restoring force. Once the distal most end of the cylindrical load bearing wall 18 is pushed past the inner proximal surface 100 of one or more retaining elements 102, the biasing restoring force may snap the one or more retaining elements 102 back to an initial position where the inner proximal surface 100 of one or more retaining elements 102 abuts the distal angled surface of the cylindrical load bearing wall 18 when the syringe 2 and plunger are place under load by the piston of the fluid injector. In this manner, a technician may install the syringe 2 into the injector by simply applying a downward force onto the syringe 2 until it snaps into the pressure jacket assembly. In certain embodiments, an audible indication, such as a click or snapping sound, may be heard as the one or more retaining elements snap closed to indicate that the syringe has been correctly installed. Snapping closed may also provide a visual indication to the technician that the syringe is correctly installed. Removal of the syringe 2 may be affected by outward movement of the one or more retaining elements 102 and corresponding retaining arms 103, either manually by the technician or by a motor of the injector. Suitable embodiments of the retaining arm mechanism are described in International PCT Application No. PCT/US2020/049885, the disclosure of which is incorporated herein by this reference.

In various embodiments, the outer diameter of the flared cylindrical load bearing wall 18 may closely abut the sidewall of the pressure jacket 104 and/or the one or more retaining elements 102 and substantially prevent entry of any spilled medical fluid, such as contrast or saline, between the cylindrical sidewall 8 of the syringe 2 and the pressure jacket 104 (see FIG. 7A). In certain embodiments, the pressurization of the syringe 2 and associated compliance due to swelling of the sidewall 8 and distal end wall 14 of the syringe 2 under pressurization may further seal the cylindrical sidewall 8 of the syringe 2 against the pressure jacket 104 and/or the one or more retaining elements 102, further increasing the sealing nature of the interaction. According to various embodiments, an elastomeric coating or material may be placed on the inner proximal surface 100 of one or more retaining elements 102 and/or on the distal surface 22 of the cylindrical load bearing wall 18 to form a fluid tight seal therebetween when the syringe closely abuts the one or more retaining elements 102.

Referring to FIGS. 1-4, the distal end 6 of the syringe 2 may further include a plurality of radial ribs 24 positioned around a periphery of the conical distal end wall 14. The plurality of radial ribs 24 extend inward from an inner edge of the cylindrical load bearing wall 18 over at least a portion of the conical distal end wall 14 towards the fluid nozzle 10. In certain embodiments, the radial ribs 24 may be provided at different lengths along the cylindrical load bearing wall 18. In other embodiments, the plurality of radial ribs may extend only a short distance along the conical distal end wall 14, for example, less than 1.5 cm. In the event shorter radial ribs 24 are used, may be easier for a user to identify one or more air bubbles in the syringe 2 since the radial ribs 24 do not significantly block the user's view into the syringe 2, for example when the fluid injector is in the upright vertical position and the natural buoyancy of the one or more air bubbles causes the air bubbles to rise toward the distal end of the conical end wall 14. According to various embodiments, the plurality of radial ribs 24 define a plurality of fluid retention channels 26 therebetween. Each fluid retention channel 26 may be located between each pair of adjacent radial ribs 24. The plurality of fluid retention channels 26 may be configured to retain a volume of liquid that has previously dripped from the fluid nozzle 10. For example, fluid in the fluid retention channels 26 will be retained within the fluid retention channels 26 when the syringe 2 is rotated from a first vertically upward facing position to a second angled downward facing position. Capillary adhesion (also known as capillary action) and surface tension of the fluid may allow the volume of liquid to be retained in the plurality of fluid retention channels 26 against the force of gravity. Further, the plurality of radial ribs 24 may abut the inner wall of the cylindrical load bearing wall 18 to further retain the fluid. For example, in certain embodiments, the syringe 2 may be filled with a fluid, such as a contrast agent, saline, or other medical fluid, with the injector head and distal end 6 of the one or more syringes 2 in the upright position, for example, for ease of filling the fluid through a spike and/or for controlling and visualizing the amount of air that is taken into the syringe 2 during a filling process. In certain embodiments, during filling through a spike or fluid path, switching between the filling fluid path and a delivery fluid path, or purging of air, a small amount of fluid may seep or drip out of the fluid nozzle 10 of the syringe 2, such as when the spike or fluid path is removed after filling or purging.

During many conventional fluid injection procedures, after the upright-configured filling process, an injector head may be rotated so that the distal ends 6 of the one or more syringes 2 are angled downward, for example to ensure that buoyancy causes any air that may remain in the syringe 2 to rise to the proximal end 4 of the syringe 2, thereby reducing the chance of air injection and embolism. For conventional syringe designs, the volume of dripped fluid may flow down an outer surface of the syringe, fouling or contaminating various surfaces of the fluid injector. In specific examples, small volumes of fluid may drip off the syringe onto the floor creating a hazard for the technician and patient, and/or contaminate various surfaces within the fluid injection suite. Further, since many contrast agents are sticky and viscous solutions, this may result in a sticky film accumulating on the flooring and other surfaces, potentially creating a safety hazard, and may further increase unnecessary contact with the contrast or other medical fluid and require additional cleaning operations.

Figure 4:
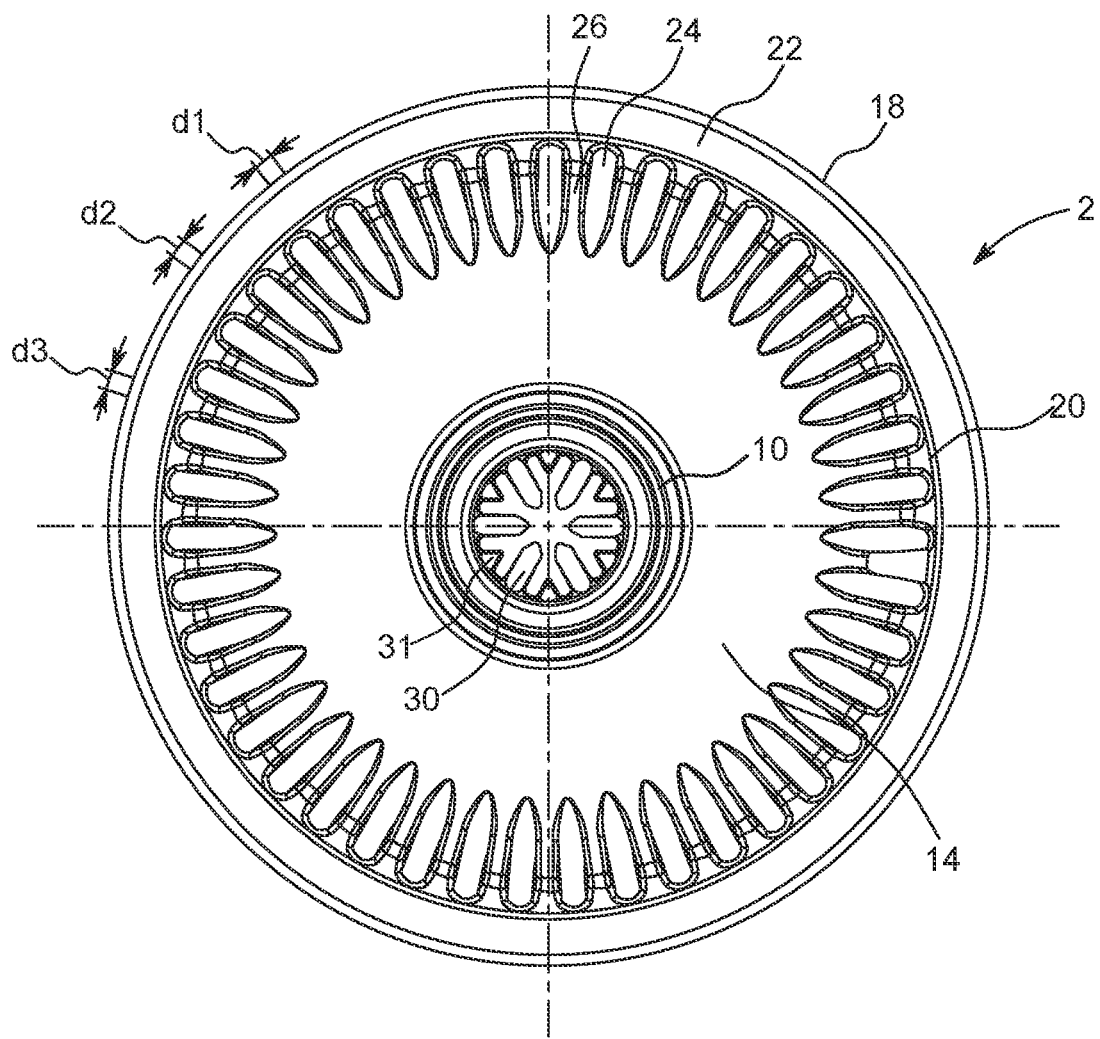
FIG. 4 is a top view of the syringe of FIG. 1.

According to various embodiments, the plurality of fluid retention channels 26 may be configured to retain the volume of liquid that has dripped from the fluid nozzle 10, for example, by capillary adhesion or action between the adjacent radial ribs 24. As illustrated in FIG. 4, the gap width between the adjacent radial ribs 24 may be referred to as d1, d2, d3, wherein some aspects the gap width is constant such that d1=d2=d3 and in other aspects the gap width is variable such that d1≠d2≠d3. In regard to the latter aspects, d1<d2<d3 or d1>d2>d3 or the appropriate gap width can be determined in some other manner, without limitation. In various embodiments, since the adjacent radial ribs 24 are arranged radially, the gap width may increase with radial distance from the central longitudinal axis L of the syringe 2. Alternatively, the gap width may remain constant by increasing the width of the radial ribs 24 with radial distance from the central axis. According to various embodiments, the distance between two adjacent radial ribs 24 which define the gap associated with the fluid retention channels 26 (i.e., "d") may range from 0.01 in to 0.25 in. Further details on capillary action are described in International PCT Publication No. WO 2017/091636, the disclosure of which is incorporated by reference herein.

According to certain embodiments, the plurality of fluid retention channels 26 may retain a maximum total volume of fluid ranging from 0.1 mL to 0.8 mL when the syringe 2 is rotated from a first upward facing position to a second angled downward facing position. Other embodiments may adjust the maximum total volume of fluid by changing the heights of the plurality of radial ribs and/or changing the distance between adjacent radial ribs. In particular embodiments, the capillary volume of fluid that the adjacent radial ribs 24 may hold is at least partially determined from the distance between each adjacent pair of the plurality of radial ribs 24, the height of each adjacent pair of the plurality of radial ribs 24, and a distance that each adjacent pair of the radial ribs 24 distally extend radially inward along the conical distal end wall 14. That is, the volume of fluid may be determined by one or more of the distance between adjacent pairs of radial ribs 24, the depth of the fluid retention channels 26 between the adjacent pairs of radial ribs 24, and the length of the adjacent pairs of radial ribs 24 and related length of the fluid retention channels 26.

In certain embodiments, at least a portion of the plurality of radial ribs 24 extend for different distances from the cylindrical load bearing wall 18 over the conical distal end wall 14. For example, in FIG. 4, the plurality of radial ribs 24 may extend from the cylindrical load bearing wall 18 over a portion of the conical distal end wall 14 of the syringe 2. In other embodiments, as illustrated in FIG. 5, the plurality of radial ribs 24 may extend from the cylindrical load bearing wall 18 up the conical distal end wall 14 of the syringe 2 toward the fluid nozzle 10 of the syringe 2.

Figure 5:
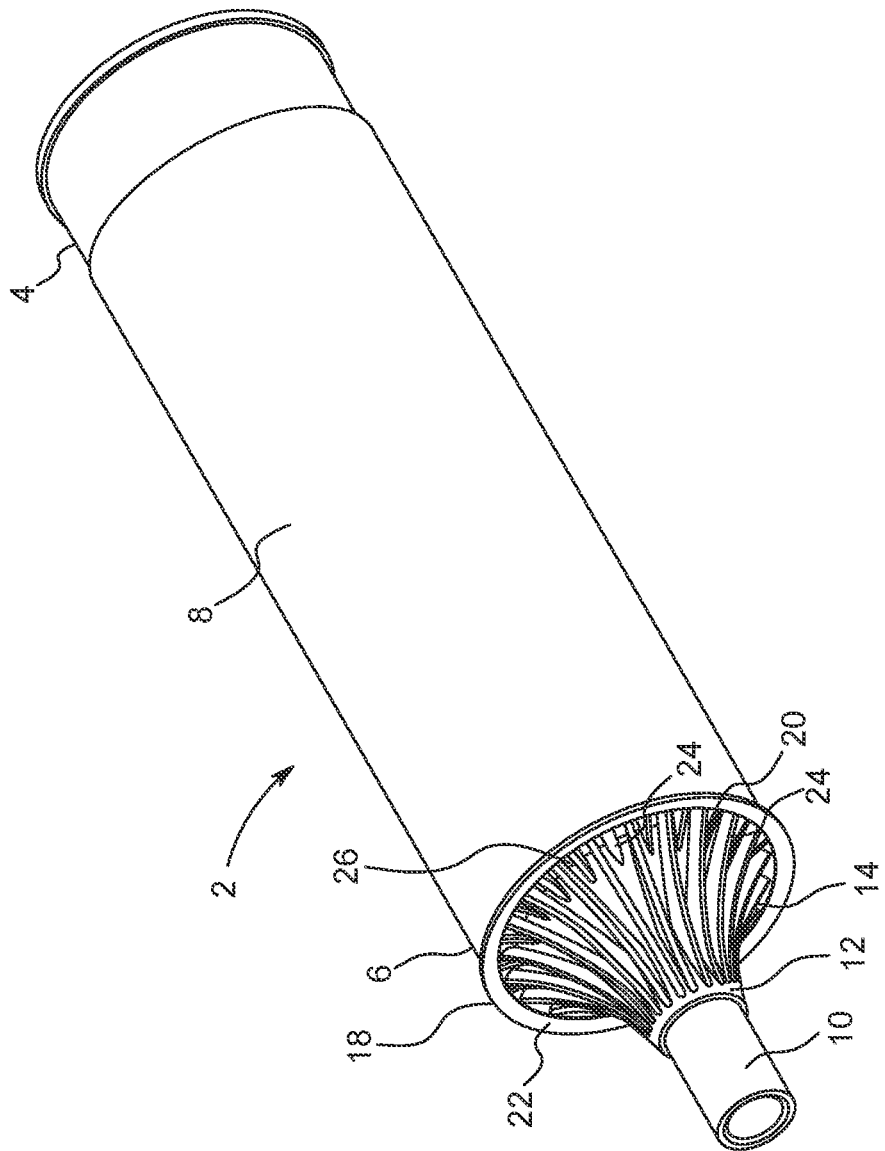
FIG. 5 is a perspective view of a syringe according to another example of the present disclosure.

As illustrated in FIG. 5, the plurality of radial ribs 24 may extend different distances from the cylindrical load bearing wall 18 and some of the radial ribs 24 may have different heights compared to others of the radial ribs 24 (see FIG. 5). As can be seen in the illustrations, in various embodiments, the plurality of radial ribs 24 abut the cylindrical load bearing wall 18 of the syringe 2, thereby forming a reservoir on the distal end 6 of the syringe 2 that assists in directing the medical fluid into the fluid retention channels 26 and also provide a further volume to retain the fluid in the reservoir having the cylindrical load bearing wall 18 as a fluid retention wall.

Figure 6:
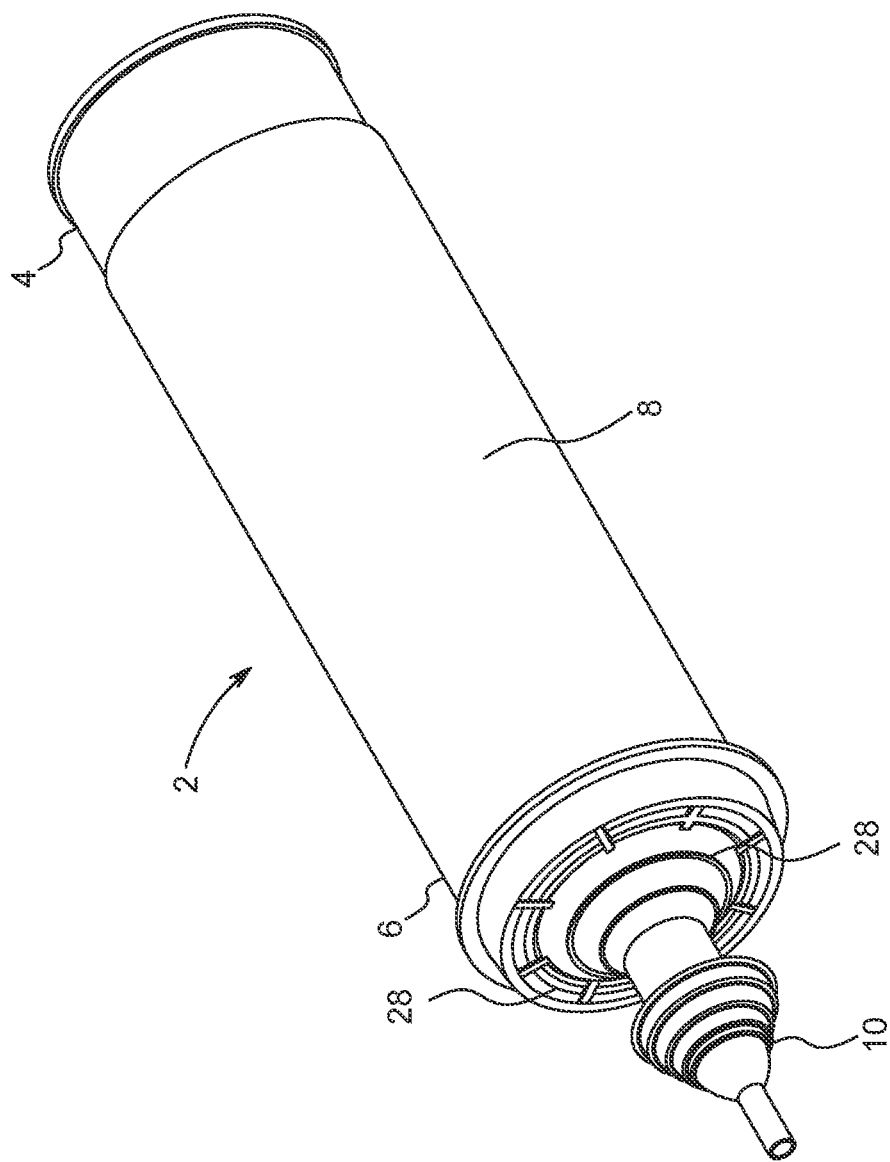
FIG. 6 is a perspective view of a syringe according to another example of the present disclosure.

In other embodiments, as shown in FIG. 6, the plurality of ribs 24 may be circumferential and arranged concentrically around the conical distal end wall 14. The concentric circumferential ribs 28 may be arranged from the cylindrical load bearing wall 18 towards the fluid nozzle 10 of the syringe 2.

In various embodiments, including the syringes 2 illustrated in FIGS. 1-6, the plurality of radial ribs 24 and/or the plurality of circumferential ribs 28 may increase a load strength of the conical distal end wall 14. For example, the plurality of radial ribs 24 or circumferential ribs 28 may provide increased thickness to the conical distal end wall 14 where the radial ribs 24 or circumferential ribs 28 are located, thereby reinforcing the strength of the conical distal end wall 14. In various embodiments, the increased wall strength may assist in withstanding and limiting compliance expansion of the conical distal end wall 14 during a pressurized fluid injection procedure. According to various embodiments, the increased thickness to the conical distal end wall 14 where the radial ribs 24 or circumferential ribs 28 are located may reduce the need for pressure jacket reinforcing of the conical distal end wall 14. For example, as illustrated in FIG. 7A, the pressure jacket 104 may be substantially cylindrical, abutting the syringe retaining elements 102, and the conical distal end wall 14 of syringe 2 may be able to withstand the high injection pressures (up to 1200 psi) without any reinforcement from the pressure jacket 104 and/or syringe retaining elements 102. This can allow easy visualization of the distal conical end wall 14 by the user, for example to check for liquid volume fill and the presence or absence of one or more air bubbles in the syringe 2.

In certain embodiments, the plurality of radial ribs 24 may increase a load strength of the cylindrical load bearing wall 18. For example, the plurality of radial ribs 24 abut and are connected to the cylindrical load bearing wall 18. This can increase the load strength of the cylindrical load bearing wall 18, for example by increasing a hoop strength of the wall. The connection between the plurality of radial ribs 24 and the cylindrical load bearing wall 18 may also increase the load strength of the cylindrical load bearing wall 18 by preventing inward or outward deformation or bending of the cylindrical load bearing wall 18 when the pressure load is applied to the syringe 2.

Figure 8:
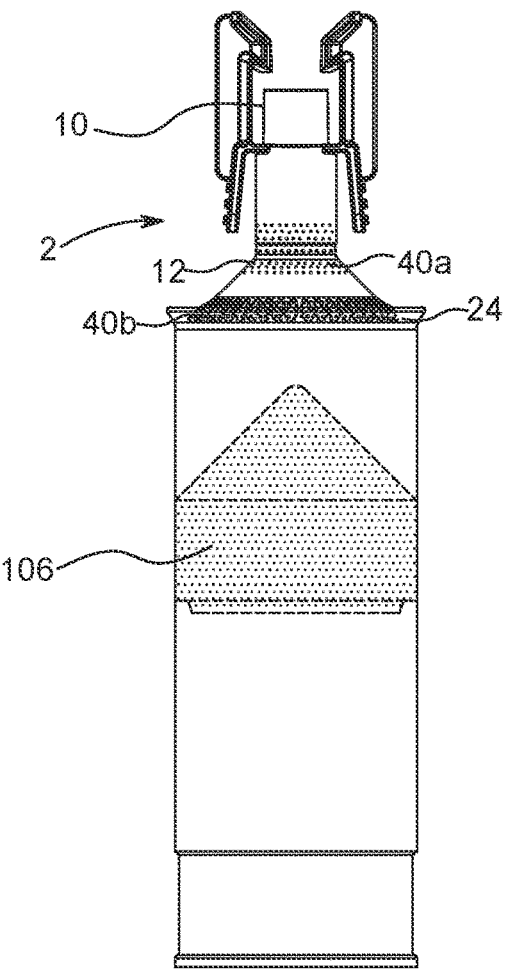
FIG. 8 is a side view of a syringe according to one example of the present disclosure.

As illustrated in FIGS. 3 and 8, according to one embodiment of the present disclosure, the proximal end 4 of the syringe 2 may have a wider diameter D1 than a diameter D2 of the remaining portion of the cylindrical sidewall 8. In this example, the "working zone" 7 of the syringe 2 wherein a plunger 106 is pushed through the fluid passageway of the cylindrical sidewall 8 may have a smaller diameter D2 compared to the diameter D1 of the "plunger storage zone" 5 at the proximal end 4. According to this embodiment, the plunger storage zone 5 is a region of the syringe where the plunger is placed during manufacturing and storage and the wider diameter D1 prevents compression of the outer circumference of the rubber plunger cover during shipping and storage. This ensures a fluid tight seal between the syringe sidewall 8 and the rubber cover of the plunger when the plunger is moved from the wider diameter D1 of the storage zone 5 to the narrower diameter D2 of the working zone 7 of syringe 2. In various embodiments of the present disclosure, a fluid injector in which the syringe 2 is held, may measure a force on a piston motor associated with pushing a plunger 106 through the fluid passageway of the syringe 2 and in particular the extra force required to move the plunger 106 from the wider diameter D1 of the storage zone 5 to the narrower diameter D2 of the working zone 7 of syringe 2. Based on the forces being applied to the piston by the fluid injector, the fluid injector may determine the size of the syringe 2 being used in the fluid injector. For example, in a longer syringe 2 that holds 200 mL of fluid, the piston may push the plunger through the proximal end 4 of the syringe 2 from the plunger storage zone 5 that has the diameter D1 into the working zone 7 that has a diameter D2. Due to D1 being larger than D2, less force is required to push the piston through the proximal end 4 of the syringe 2 than through the working zone 7 of the syringe 2. Therefore, the fluid injector may calibrate the piston position for when the plunger 106 is pushed into the working zone 7 of the syringe 2 based on the change in force applied to the piston when moving from the storage zone 5 at the proximal end 4 with the diameter D1 to the working zone 7 with the diameter D2. For longer, larger volume syringes that have a larger working zone 7, the change in force applied to the piston will occur at a predetermined piston position corresponding to the closeness of the proximal end 4 of the syringe 2 to the injector head, whereas for shorter, smaller volume syringes that have a smaller working zone 7 (for example, 100 mL or 50 mL) that will be positioned more distally in the pressure jacket (i.e., when the distal end 6 of syringe 2 abuts the syringe retaining element 102), the change in force applied to the piston will occur at a predetermined piston position where the piston is extended farther along the piston path, corresponding to the fact that the proximal end 4 and plunger of the syringe 2 is farther away from the injector head in the initial position.

The position where the fluid injector registers the change in force applied to the piston due to moving the plunger from the storage zone 5 to the working zone 7 may allow the injector to determine the length and thus, the volume of the syringe that has been loaded into the pressure jacket and make various adjustments to any programmed injection procedure according to this information. Further, if the fluid injector notes that the piston force change does not occur or otherwise notes a deviation in an expected position of the force change, the fluid injector may stop the fluid injection procedure and notify the technician that an error has occurred. For example, if a syringe is inadvertently being reused, the plunger will likely not be in the initial storage zone 5 and the position of the force change will not be in the expected position, thus allowing the fluid injector to notify the technician and prevent inadvertent re-use of a syringe. Likewise, if the plunger has been inadvertently moved into the working zone 7, for example during shipping, the fluid injector will note that the force change is missing and prevent use of a potentially damaged syringe (e.g., where the fluid seal between the plunger and syringe sidewall may be compromised).

In other embodiments, as shown in FIG. 7A, the cylindrical load bearing wall 18 may have a distal surface 22 configured for interfacing and abutting with a proximal surface 100 of a syringe retaining elements 102 of the syringe retention arms 103 of the fluid injector. According to specific embodiments, the distal surface 22 of the cylindrical load bearing wall 18 may be radially angled such that the inner circumferential edge of the distal surface 22 is proximal along the longitudinal axis relative to the outer circumferential edge of the distal surface 22. According to this embodiment, the corresponding proximal surface 100 of the syringe retaining elements 102 is radially angled in the complementary similar direction than the radial angle of distal surface 22 of the cylindrical load bearing wall 18. According to various embodiments, the angle of the distal surface 22 may range from 1° to 89° and in particular embodiments from 1° to 30° with the angle of the corresponding proximal surface 100 being complementary. As such, when the radially angled distal surface 22 of the cylindrical load bearing wall 18 interfaces with the corresponding radially angled proximal surface 100 of the syringe retaining elements 102 when the syringe 2 is under load during a delivery process, the two surfaces 22 and 100 interact as the pressurized syringe 2 is urged in the distal direction along the longitudinal axis L such that a retaining force is established on the retention arms 103 that urges the retaining arms 103 radially inward to maintain the closed configuration. As such, the forces retaining the syringe 2 within the pressure jacket 104 and the retention mechanism of the fluid injector is increased during a pressurized delivery of fluid during a contrast injection procedure. In one non-limiting example, as the syringe 2 is inserted into the fluid injector, the cylindrical load bearing wall 18 may be configured to move the retaining arms 103 outwardly to open the retaining arms 103 to allow the syringe 2 to move into the fluid injector. After the syringe 2 has moved past the syringe retaining elements 102, the retaining arms 103 may be configured to move inwardly to close in on one another to retain the syringe 2 in the fluid injector.

Figure 9:
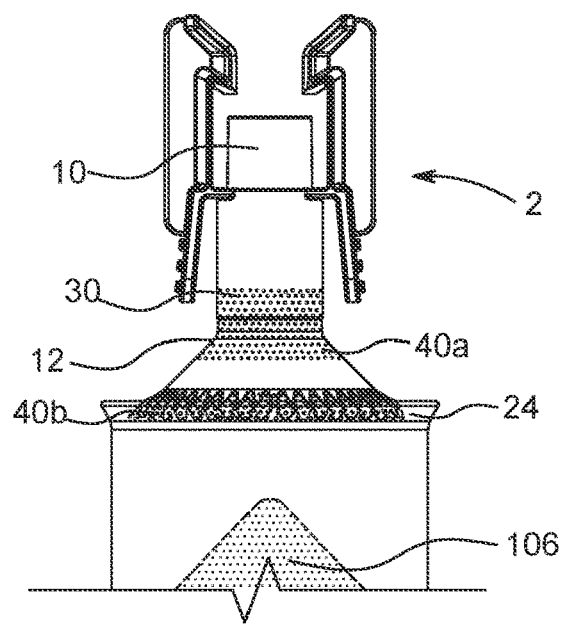
FIG. 9 is a close-up side view of distal tip of the syringe of FIG. 8.

As described in U.S. Pat. No. 10,420,902, the disclosure of which is incorporated by this reference, and shown in FIGS. 8 and 9, the presence of small amounts of air (up to 5% of total volume of syringe) in the syringe 2 may be visualized by the presence or absence of an illuminated halo 40a at the conical distal end 6 of the syringe 2. For example, electromagnetic radiation may be reflected and refracted from a colored surface or shown through a translucent or transparent plunger cap (from light sources in the piston head). If the syringe 2 is fully filled with a liquid fluid, the electromagnetic radiation will refract/reflect against the syringe sidewall 8 and conical distal end wall 14 to show a refraction halo effect in the form of an illuminated halo 40a around the circumference of the distal portion of the conical distal end 6 of the syringe 2. In the presence of small amounts of air (for example up to 5 mL or more), the illuminated halo 40a is not observed. This provides a method for a technologist to visually determine if there is air in the syringe 2 and perform a purge/prime operation to remove the air and prevent injection of air into the patient. In certain embodiments, the visualization process may also be performed by the injector when fitted with an appropriate camera and associated software. According to various embodiments of the present disclosure, at least one of the cylindrical load bearing wall 18 and the plurality of radial ribs 24 may enhance an amount of electromagnetic radiation refracted at the distal end 6 of the syringe 2 when the syringe 2 is filled with a liquid. For example, the plurality of radial ribs 24 may act similar to a Fresnel lens and increase the reflection/refraction of the electromagnetic radiation creating a brighter illuminated halo at the around the circumference of the distal portion of the conical distal end 6 of the syringe 2. In other embodiments, the electromagnetic radiation may also reflect back from the distal conical end and illuminate a halo 40b around at least a portion of the cylindrical load bearing wall 18, for example around the plurality of radial ribs 24. In specific embodiments, the electromagnetic radiation may be emitted from at least one electromagnetic radiation source in a piston head of a fluid injector. In other embodiments, the electromagnetic radiation may be reflected from at least a portion of a surface of a plunger 106 of a syringe 2.

In certain embodiments, the syringes 2 of the present disclosure may include one or more features that improve fluid flow into and out of the syringe 2 during fluid fill and fluid delivery processes. According to various embodiment, the syringe 2 may include a neck associated with the fluid nozzle 10 at the distal end 6 of the syringe 2. The neck may include a larger diameter than conventional syringes, for example to include a connector element as described in International PCT Application No. PCT/US2021/018523. The neck of syringe 2 may include a fluid passageway having a plurality of fluid diverting ribs 30 extending radially inward from an inner surface of the neck at least partially into the fluid passageway, as illustrated in FIGS. 3 and 4.

According to various embodiments, the plurality of fluid diverting ribs 30 may divert a fluid flowing through the fluid nozzle 10 into the syringe 2 during a filling procedure so that the fluid flows along internal surfaces of the conical distal end wall 14 and the cylindrical sidewall 8 of the syringe 2. In certain embodiments, the plurality of fluid diverting ribs 30 may include ribs extending radially inward for different distances (compare ribs 30 and 31 in FIG. 4) and/or extend for different lengths along the longitudinal axis L of the fluid nozzle 10. While not intending to be limited by any interpretation, the redirection of fluid flow through the syringe fluid nozzle 10 is believed to be a result of a Coanda effect, where the fluid diverting ribs 30 result in the fluid adhering to the internal sidewall of the conical distal end wall 14 and the cylindrical sidewall 8 of the syringe 2. For example, capillary adhesion of the fluid against the walls of the fluid diverting ribs 30 may allow surface tension to hold the fluid against the internal sidewalls of the neck and continue into the internal sidewall of the conical distal end wall 14 and the cylindrical sidewall 8. Flowing the fluid down the inner sidewalls of the syringe instead of allowing the fluid to flow into the syringe without contacting the inner sidewalls results in fewer air bubbles in the fluid during the filling procedure. In contrast, with conventional syringes without fluid diverting ribs 30, the fluid may flow/drip down the middle of the syringe fluid nozzle 10 and drip to the plunger 106 resulting in formation of air bubbles in the fluid. These air bubbles may adhere to the plunger 106 and sidewall surfaces and are typically difficult to remove during a priming sequence. The resulting air bubbles may increase the chances of air embolism by injection of small amounts of air, particularly in angiography procedures. As noted, particularly with high pressure CV imaging procedures, any air bubbles in the syringe and/or fluid path must be avoided to prevent air embolism. According to these embodiments, the fluid diverting ribs 30 minimize an amount of air bubbles in the fluid in the syringe 2. Previous work had shown that a fluid diverter in the middle of the flow path through the nozzle reduces bubble formation during fill, see for example International PCT Publication No. WO2017091643 the disclosure of which is incorporate by reference herein. The described fluid diverting ribs 30 provide a similar effect without the need for a fluid diverter feature in the flow path, thus simplifying manufacture and injection molding of the syringe 2. The amount of air bubbles in the fluid in the filled syringe 2 may be minimized by the fluid flowing along the internal surfaces of the distal end wall 14 and the cylindrical sidewall 8 of the syringe 2, rather than dripping/flowing directly from the syringe fluid nozzle 10 to the plunger surface. In one embodiment of the present disclosure, the fluid diverting ribs 30 may also increase the illuminated circumferential halo effect described herein to identify whether air bubbles are present in the syringe 2. As observed with the plurality of radial ribs 24, the fluid diverting ribs 30 may magnify and further reflect/refract incident electromagnetic radiation, increasing the brightness of the observed illuminated halo at the around the circumference of the distal portion of the conical distal end 6 of the syringe 2. In specific embodiments, at least a portion of the plurality of fluid diverting ribs 30 may have different cross-sectional profiles. In other embodiments, at least a portion of the plurality of fluid diverting ribs 30 may extend from the inner surface of the fluid nozzle 10 for different distances into the distal portion of the conical distal end 6 of the syringe 2.

According to various embodiments, the plurality of fluid diverting ribs 30 may also allow for increased filling speeds, for example potentially due to more laminar flow of the fluid into the syringe 2 as the fluid passes the fluid diverting ribs 30. Thus, the time between procedures may be substantially decreased as the syringes may be filled faster than conventional syringes. In addition, the fill rate may be increased since the formation of bubbles during filling is reduced, resulting in smaller prime volumes and lower production of waste fluids associated with greater prime volumes.

According to various embodiments, the presently described features may increase the ease of injection molding a syringe 2. For example, syringes 2 may be formed from a medical grade plastic, such as PET, polycarbonate, polyethylene, and blends thereof, and may be formed into the syringe shape by an injection molding process. During injection molding, features may cause issues during removal of the item from the mold, such as the presence of undercuts due to the features. Further, certain features may require specific and expensive mold configurations that may still result in high rejection rates. According to various embodiments of the syringe 2 and features described therewith, the configuration of the plurality of radial ribs 24, the fluid diverting ribs 30, and the cylindrical load bearing wall 18 may eliminate undercuts from an injection mold for injection molding the syringe 2.

Multiple beneficial features for a syringe 2 are described in the present disclosure. It is noted that various combinations of the described features may be incorporated into a syringe as required by the intended use of the syringe and the features of the fluid injector. For example a syringe may include at least one of the features and may include various other described features as necessary. For example, according to an embodiment, a syringe may include a plurality of radial ribs 24 around the periphery of the conical distal end wall 14 and a cylindrical load bearing wall 22 as described herein but not include a plurality of fluid diverting ribs 30. According to another embodiment, a syringe may include a plurality of radial ribs 24 around the periphery of the conical distal end wall 14, a cylindrical load bearing wall 22, and a plurality of fluid diverting ribs 30 as described herein. According to another embodiment, a syringe may include, a cylindrical load bearing wall 22, and a plurality of fluid diverting ribs 30 but not the plurality of radial ribs 24 as described herein. Thus, the various embodiments described in detail herein and illustrate in the attached figures are for illustration purposes only and are in no way limiting to the features incorporated into the syringe.

While various aspects of the syringe assembly and various features have been described in the context of syringes for powered medical injectors, the syringe assembly and various features described herein may also be incorporated into handheld syringes for delivering fluids at low injection pressures. For example, in many medical settings where a fluid is to be injected by a handheld syringe, the physician may draw a fluid into the syringe from a corresponding fluid container, such as a vial, and then may prime or purge the syringe of any air by holding the syringe in a vertical position and pressing on the plunger assembly to deliver a small amount of the fluid along with any air contained within the syringe. The ejected fluid may drip down the side of the needle and the syringe body, potentially exposing the physician to contact with the medical fluid. The syringe assembly and various features described herein may be utilized on a handheld syringe to prevent drips of the fluid, either that ejected during the priming process or fluid drips during an injection process, from contacting the physician or dripping onto surfaces. Handheld syringes comprising various embodiments of the syringe assembly and various features are within the scope of this disclosure.

Still other aspects of the present disclosure relate to other medical devices comprising the syringe assembly and various features described herein. For example, any medical devices that deliver fluids which may include leaking or dripping of small amounts of fluid from a fluid aperture to a surface thereof may benefit from the fluid wicking flanges of the present disclosure. Examples of such medical devices include, but are not limited to, catheters (such as the distal end or those portions positioned immediately outside the patient's body), tubing sets, IV lines, tubing connectors and clips, shunts, fluid manifolds, valves, aspiration tubing, surgical tools, pump fluid outputs, and the like may all be modified to include the various features described herein.

It is worthy to note that any reference to "one aspect" or "an aspect" means that a particular feature, structure, or characteristic described in connection with the aspect is included in at least one aspect. Thus, appearances of the phrases "in one aspect" or "in an aspect" in various places throughout the specification are not necessarily all referring to the same aspect. Furthermore, the particular features, structures, or characteristics may be combined in any suitable manner in one or more aspects.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

With respect to the use of any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, other different components. It is to be understood that such depicted architectures are merely exemplary, and that, in fact, many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include, but are not limited to, physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "operative," "adapted," etc. Those skilled in the art will recognize that "configured to" can generally encompass active-state components, and/or inactive-state components, and/or standby-state components, unless context requires otherwise.

While particular aspects of the subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be understood to include the possibilities "A" or "B" or "A and B."

In summary, numerous benefits have been described which result from employing the concepts described herein. The foregoing disclosure has been presented for purposes of illustration and description. It is not intended to be exhaustive or limiting to the precise form disclosed. Modifications or variations are possible in light of the above teachings. It is intended that the claims submitted herewith define the overall scope of the present disclosure.

We claim:

1. A syringe comprising:
a proximal end, a distal end, and a cylindrical sidewall extending between the proximal end and the distal end, wherein the distal end comprises a conical distal end wall and a fluid nozzle at a distal end of the conical distal end wall;
a cylindrical load bearing wall extending axially from the cylindrical sidewall past a proximal end of the conical distal end wall, wherein the cylindrical load bearing wall extends axially from the cylindrical sidewall of the syringe and wherein the cylindrical load bearing wall extends radially outward from the cylindrical sidewall of the syringe at an angle of from 1 degree to 30 degrees relative to a longitudinal axis of the syringe; and
a plurality of radial ribs positioned around a periphery of the conical distal end wall, wherein a longitudinal axis of the plurality of radial ribs extends radially inward from the cylindrical load bearing wall towards the fluid nozzle over at least a portion of the conical distal end wall.

2. The syringe of claim 1, wherein the plurality of radial ribs defines a plurality of fluid retention channels, wherein a fluid retention channel of the plurality of fluid retention channels is located between each pair of adjacent radial ribs of the plurality of radial ribs, wherein the plurality of fluid retention channels is configured to retain a volume of liquid by capillary adhesion.

3. The syringe of claim 2, wherein the volume of liquid retained by the plurality of fluid retention channels ranges from 0.1 to 0.8 milliliters.

4. The syringe of claim 1, wherein the plurality of radial ribs increase a load strength of the conical distal end wall.

5. The syringe of claim 1, wherein the plurality of radial ribs increase a load strength of the cylindrical load bearing wall.

6. The syringe of claim 1, wherein the cylindrical load bearing wall is configured to abut a retaining surface of a retaining arm of a fluid injector to retain the syringe within a pressure jacket during a pressurized injection procedure.

7. The syringe of claim 1, wherein a distal surface of the cylindrical load bearing wall is angled radially from a more proximal inner portion to a more distal outer portion relative to the longitudinal axis of the syringe.

8. The syringe of claim 7, wherein the angle of the distal surface of the cylindrical load bearing wall is configured to prevent entry of fluid between the cylindrical sidewall of the syringe and a pressure jacket in which the syringe is placed.

9. The syringe of claim 7, wherein the angle of the distal surface of the cylindrical load bearing wall is configured to increase a radially inward force on a retaining arm of a fluid injector.

10. The syringe of claim 1, wherein at least one of the cylindrical load bearing wall and the plurality of radial ribs is configured to enhance a refraction halo effect at a distal portion of the conical distal end wall of electromagnetic radiation emitted from at least one electromagnetic radiation source in a piston or plunger head of a fluid injector.

11. The syringe of claim 1, further comprising a neck associated with the fluid nozzle at the distal end of the conical distal end wall, wherein the neck includes a fluid passageway having a plurality of longitudinal fluid diverting ribs extending radially inward at least partially into the fluid passageway from an inner surface of the neck.

12. The syringe of claim 11, wherein the plurality of longitudinal fluid diverting ribs is configured to divert a fluid flowing through the fluid passageway of the neck into the syringe so that the fluid flows along an internal surface of the conical distal end wall and an internal surface of the cylindrical sidewall of the syringe.

13. The syringe of claim 11, wherein at least a portion of the plurality of longitudinal fluid diverting ribs have different profiles.

14. The syringe of claim 11, wherein at least a portion of the plurality of longitudinal fluid diverting ribs extend from the inner surface of the neck at different distances into the fluid passageway.

15. The syringe of claim 1, wherein the plurality of radial ribs extend along the conical distal end wall at an angle relative to the longitudinal axis of the syringe such that a distance between each adjacent pair of the plurality of radial ribs tapers from the cylindrical load bearing wall toward the fluid nozzle.

* * * * *

UNITED STATES PATENT AND TRADEMARK OFFICE
CERTIFICATE OF CORRECTION

| | | |
|---|---|---|
| PATENT NO. | : 12,048,835 B2 | Page 1 of 1 |
| APPLICATION NO. | : 18/041104 | |
| DATED | : July 30, 2024 | |
| INVENTOR(S) | : Spohn et al. | |

It is certified that error appears in the above-identified patent and that said Letters Patent is hereby corrected as shown below:

In the Specification

In Column 10, Line 28, delete "distal most" and insert -- distalmost --, therefor.
In Column 10, Line 36, delete "place" and insert -- placed --, therefor.
In Column 12, Line 10, delete "wherein" and insert -- wherein in --, therefor.
In Column 12, Line 24, delete "in to" and insert -- in. to --, therefor.
In Column 15, Line 59, delete "at the around" and insert -- around --, therefor.
In Column 17, Line 7, delete "at the around" and insert -- around --, therefor.

Signed and Sealed this
Fourth Day of March, 2025

Coke Morgan Stewart
*Acting Director of the United States Patent and Trademark Office*